United States Patent
Atkins et al.

(10) Patent No.: US 10,723,673 B2
(45) Date of Patent: *Jul. 28, 2020

(54) OLIGOMERISATION PROCESS

(71) Applicant: Petroliam Nasional Berhad (Petronas), Kuala Lumpur (MY)

(72) Inventors: Martin Philip Atkins, Antrim (GB); Kenneth Richard Seddon, Antrim (GB); Malgorzata Swadzba-Kwasny, Antrim (GB); Fergal Coleman, Antrim (GB)

(73) Assignee: PETROLIAM NASIONAL BERHAD (PETRONAS), Kuala Lumpur (MY)

( * ) Notice: Subject to any disclaimer, the term of this patent is extended or adjusted under 35 U.S.C. 154(b) by 0 days.

This patent is subject to a terminal disclaimer.

(21) Appl. No.: 14/783,369

(22) PCT Filed: Apr. 9, 2014

(86) PCT No.: PCT/GB2014/051115
§ 371 (c)(1),
(2) Date: Oct. 8, 2015

(87) PCT Pub. No.: WO2014/167332
PCT Pub. Date: Oct. 16, 2014

(65) Prior Publication Data
US 2016/0052838 A1 Feb. 25, 2016

(30) Foreign Application Priority Data
Apr. 10, 2013 (GB) .................................. 1306553.7

(51) Int. Cl.
*C07C 2/22* (2006.01)
*B01J 31/02* (2006.01)
(Continued)

(52) U.S. Cl.
CPC ............ *C07C 2/22* (2013.01); *B01J 31/0249* (2013.01); *B01J 31/143* (2013.01);
(Continued)

(58) Field of Classification Search
CPC ...................................................... C07C 2/22
(Continued)

(56) References Cited

U.S. PATENT DOCUMENTS 2,085,535 A * 6/1937 Langedijk ................ C07C 2/20
585/507
2,697,694 A * 12/1954 Harold Shalit ......... C08F 10/00
585/519
(Continued)

FOREIGN PATENT DOCUMENTS

GB        1388224 A  *  3/1975  ............... C07C 2/22

OTHER PUBLICATIONS

Francis, A. W. "Solutions of Aluminum Chloride as Vigorous Catalysts", Ind. Eng. Chem., (1950), pp. 342-344.*
(Continued)

*Primary Examiner* — Philip Y Louie
(74) *Attorney, Agent, or Firm* — Ryan T. Grace; Advent, LLP

(57) ABSTRACT

A process is provided for the selective oligomerisation of C5 to C20 alpha-olefins to produce polyalphaolefin oligomers with a molecular weight distribution that is suitable for use in lubricant base oils.

20 Claims, 15 Drawing Sheets

(51) Int. Cl.
    *B01J 31/14*     (2006.01)
    *C10M 105/04*    (2006.01)
(52) U.S. Cl.
    CPC ........ *C10M 105/04* (2013.01); *B01J 2231/20* (2013.01); *B01J 2531/31* (2013.01); *B01J 2531/32* (2013.01); *C07C 2527/125* (2013.01); *C07C 2527/126* (2013.01); *C07C 2527/16* (2013.01); *C07C 2527/20* (2013.01); *C07C 2527/24* (2013.01); *C07C 2527/26* (2013.01); *C07C 2531/14* (2013.01); *C10M 2203/022* (2013.01)
(58) Field of Classification Search
    USPC .......................................... 585/511, 521, 520
    See application file for complete search history.

(56)            References Cited

U.S. PATENT DOCUMENTS

| 3,842,134 | A |   | 10/1974 | Pratt |           |
|-----------|---|---|---------|-------|-----------|
| 3,957,664 | A |   | 5/1976  | Heilman et al. | |
| 4,066,715 | A |   | 1/1978  | Isa et al. | |
| 4,650,917 | A | * | 3/1987  | Dessau | C10G 69/126 |
|           |   |   |         |       | 208/310 Z |
| 4,709,007 | A | * | 11/1987 | Jansons | C08G 61/127 |
|           |   |   |         |       | 528/222 |
| 4,879,366 | A |   | 11/1989 | Jansons et al. | |
| 4,926,004 | A | * | 5/1990  | Pelrine | B01J 23/92 |
|           |   |   |         |       | 585/10 |
| 5,910,619 | A | * | 6/1999  | Urata | C07C 2/32 |
|           |   |   |         |       | 585/500 |
| 6,127,301 | A | * | 10/2000 | Iwanaga | B01J 31/0241 |
|           |   |   |         |       | 502/119 |
| 2011/0054209 | A1 | * | 3/2011 | De Kraker | C07C 2/34 |
|           |   |   |         |       | 560/129 |

OTHER PUBLICATIONS

Galova, M.; Lux, L. "The study of aluminum halides in nonaqueous solvents. I. Basic polarographic characteristics", Chem. zvesti, 29 (3), pp. 279-289 (1975).*
Hinton, J.F.; Amis, E.S. "Solvation in Aqueous N-Methylacetamide Solutions of Aluminium Chloride: an N.m.r. Study", Chem. Comm. (1967); pp. 100-101.*
International Search Report dated Jul. 18, 2014 for PCT/GB2014/051115.
Search Report Under Section 17 dated Oct. 10, 2013 for Appln. No. GB1306553.7.

* cited by examiner

OLIGOMERISATION PROCESS

This invention relates to base oils for lubricating compositions. In particular, the present invention provides a process for the selective oligomerisation of $C_5$ to $C_{20}$ alpha-olefins to produce polyalphaolefin oligomers with a molecular weight distribution that is suitable for use in lubricant base oils.

Lubricant compositions generally comprise a base oil of lubricating viscosity together with one or more additives to deliver properties such as reduced friction and wear, improved viscosity index, detergency, and resistance to oxidation and corrosion. A lubricant base oil may comprise one or more sources of lubricating oil, referred to as base stocks.

Lubricant base stocks useful in automotive engine lubricants may be obtained as higher boiling fractions from the refining as crude oil or via synthetic routes, and are classified as Group I, II, III, IV and V base stocks according to API standard 1509, "ENGINE OIL LICENSING AND CERTIFICATION SYSTEM", April 2007 version 16th edition Appendix E. Group IV refers to polyalphaolefin (PAO) base stocks, which are typically synthesised by oligomerisation of 1-decene. The principal component of these base stocks is decene trimer, although the dimer, tetramer and pentamer are typically also present in the various base stock blends.

A number of catalytic processes are currently in use for the oligomerisation of alpha-olefins to produce lubricant base stocks.

Ziegler-Natta catalysts are a class of catalysts that comprise titanium compounds in combination with an organoaluminium compound. Typically, Ziegler-Natta catalysts used commercially for the polymerisation of alpha-olefins comprise a titanium complex (such as $TiCl_4$) together with an organoaluminium compound (such as triethylaluminium) on a magnesium chloride support.

Metallocene complexes (such as dicyclopentadienylzirconium dichloride, $Cp_2ZrCl_2$) have also been used as catalysts for the oligomerisation of alpha-olefins in combination with a methylaluminoxane activator.

It is also known that Lewis acids such as $BF_3$, $AlCl_3$ and $EtAlCl_2$ can be used as catalysts for cationic polymerisation of alpha-olefins in conjunction with an alkyl halide (for instance tert-butyl chloride), alcohol or Brønsted acid.

U.S. Pat. No. 7,527,944 discloses the use of ionic liquids as catalysts for the cationic polymerisation of alpha-olefins. Ionic liquids are a class of compounds that have been developed over the last few decades. The term "ionic liquid" as used herein refers to a liquid that can be obtained by melting a salt, and which is composed entirely of ions. The term "ionic liquid" includes compounds having both high melting points and compounds having low melting points, e.g. at or below room temperature. Ionic liquids having melting points below around 30° C. are commonly referred to as "room temperature ionic liquids" and are often derived from organic salts having nitrogen-containing heterocyclic cations, such as imidazolium and pyridinium-based cations.

The ionic liquid catalysts disclosed by U.S. Pat. No. 7,572,944 comprise pyridinium or imidazolium cations together with chloroaluminate anions. The use of ionic liquids as polymerisation catalysts is known to provide certain advantages over conventional catalysts. In particular, ionic liquids are generally immiscible with hydrocarbons and thus can be separated from polyalphaolefin products by phase separation and recycled. In contrast, conventional Lewis acid catalysts are generally quenched during the isolation of products.

However, a disadvantage of ionic liquid systems is that the organic cations are spectator ions which play no part in the catalytic reaction, other than to moderate the melting point of the ionic liquid reaction medium. The organic cations commonly used in ionic liquids are generally expensive, and require additional synthetic steps to prepare the desired cation from commercially available precursors. Specifically, it is usually necessary to prepare an ionic liquid of the formula [cation]$^+$Cl$^-$ in a first step, followed by a second step in which the chloride ionic liquid is converted to a chloroaluminate ionic liquid by reaction with $AlCl_3$. It would therefore be desirable to identify new systems which may be prepared more easily and with less expense than chloroaluminate ionic liquids.

A further disadvantage of ionic liquid systems, in common with other Lewis acid catalysts, is that the catalysts are extremely active and thus tend to form undesired highly oligomerised products, thereby wasting resources. While the use of dopants to moderate the Lewis acidity of chloroaluminate ionic liquid systems has been investigated, these provide in general only modest improvements.

Accordingly, there is a need in the art for new processes for the production of polyalphaolefin oligomers which overcome one or more of the disadvantages of the processes that are known in the art.

In a first aspect, the present invention provides a process for the preparation of alpha-olefin oligomers, comprising contacting an olefinic feedstock comprising $C_5$ to $C_{20}$ alpha-olefins with a liquid complex catalyst comprising:
(i) at least one metal halide salt of the formula $MX_3$, wherein M is selected from aluminium and gallium, and each X is independently selected chlorine, bromine and iodine; and
(ii) at least one Lewis basic donor ligand containing a donor atom selected from oxygen, sulphur, nitrogen, phosphorus, arsenic and selenium;
wherein the molar ratio of the at least one metal halide salt to the at least one Lewis basic donor ligand is in the range of from 1:1 to 4:1.

As used herein, the term "liquid complex" or "LC" refers to a class of liquids that is composed of metallate cations and anions in equilibrium with neutral species. Liquid complexes are obtained by combining neutral donor molecules with Al(III) or Ga(III) halides. Without being bound by any specific theory, it is understood from spectroscopic studies that the addition of a donor ligand to Al(III) or Ga(III) halides causes disproportionation of the metal species into cationic and anionic complexes which exist in equilibrium with neutral complexes, according to the following general schemes (wherein L represents a Lewis basic donor ligand and $\chi_{MX_3}$ indicates the mole fraction of $MX_3$):

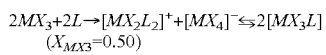
$$2MX_3 + 2L \rightarrow [MX_2L_2]^+ + [MX_4]^- \leftrightarrows 2[MX_3L]$$
$(\chi_{MX_3} = 0.50)$

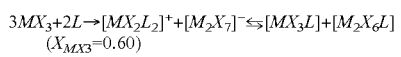
$$3MX_3 + 2L \rightarrow [MX_2L_2]^+ + [M_2X_7]^- \leftrightarrows [MX_3L] + [M_2X_6L]$$
$(\chi_{MX_3} = 0.60)$

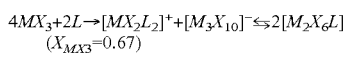
$$4MX_3 + 2L \rightarrow [MX_2L_2]^+ + [M_3X_{10}]^- \leftrightarrows 2[M_2X_6L]$$
$(\chi_{MX_3} = 0.67)$ FIG. 1 shows a portion of the $^{27}$Al NMR spectra obtained for liquid complexes comprising $AlCl_3$ and acetamide at a molar ratio of 1:1 ($\chi_{AlCl_3} = 0.50$) and 3:2 ($\chi_{AlCl_3} = 0.60$). The peaks identified in the spectrum correspond to the cationic, anionic and neutral species described above.

Liquid complexes are thus distinct from chlorometallate ionic liquids, which consist only of ions, whereas LCs are believed to comprise ionic species in equilibrium with neutral species. Furthermore, the active Lewis acidic catalytic species in chloroaluminate ionic liquids is always the [$Al_2Cl_7$]⁻ anion, and only its concentration in the ionic liquid can be manipulated. In contrast, in LCs, the reactivity of the system depends on the ligands selected and on the molar ratio of ligands to the metal halide salt ($\chi_{MX3}$). Accordingly, LCs provide much greater scope for modulating the reactivity of the system compared to chloroaluminate ionic liquids.

The present inventors have surprisingly found that the use of liquid complexes as defined above as catalysts for the oligomerisation of $C_5$ to $C_{20}$ alpha-olefins provides an oligomerised product with a molecular weight distribution that is particularly suitable for use as a lubricant base stock, i.e. consisting predominantly of dimers, trimers, tetramers and pentamers, and with only low levels of undesired highly oligomerised products. The liquid complexes are also immiscible with the oligomeric product and thus can readily be separated from the product by phase separation. Furthermore, separation of the liquid complexes from the oligomeric product is non-destructive for the liquid complexes, which can therefore be recycled to the oligomerisation reaction without the need for purification or regeneration steps. Still a further advantage of the liquid complex systems of the present invention is that cheap, widely available Lewis donor ligands such as urea, thiourea, acetamide and dimethylsulfoxide may be used to prepare the liquid complexes, thus providing a significant cost saving in comparison to the use of expensive ionic liquid cations as described above.

Where M represents aluminium, the molar ratio of the at least one metal halide salt to the at least one Lewis basic donor ligand is preferably in the range of from 1:1 to 2:1.

More preferably, where M represents aluminium, the molar ratio of the at least one metal halide salt to the at least one Lewis basic donor ligand is from about 55:45 ($\chi_{MX3}$=0.55) to about 65:35 ($\chi_{MX3}$=0.65). Still more preferably, where M represents aluminium, the molar ratio of the metal halide salt to the at least one Lewis basic donor ligand is about 3:2 ($\chi_{MX3}$=0.60).

Where M represents gallium, the molar ratio of the metal halide salt to the at least one Lewis basic donor ligand is preferably in the range of from 1:1 to 3:1.

More preferably, where M represents gallium, the molar ratio of the gallium halide salt to the at least one Lewis basic donor ligand is from about 55:45 ($\chi_{MX3}$=0.55) to about 75:25 ($\chi_{MX3}$=0.65). Still more preferably, where M represents gallium, the molar ratio of the gallium halide salt to the at least one Lewis basic donor ligand is about 3:2 ($\chi_{MX3}$=0.60).

In preferred embodiments, M represents aluminium.

X preferably represents bromine or chlorine. Most preferably, X represents chlorine.

In further preferred embodiments $MX_3$ is selected from $AlCl_3$ and $GaCl_3$. Most preferably, $MX_3$ represents $AlCl_3$.

In some embodiments of the invention, the metal halide salt having the formula $MX_3$ may optionally comprise two or more salts having the formula $MX_3$.

The at least one Lewis basic donor ligand is preferably selected from small molecule donor ligands having a molecular weight of 500 or less, preferably a molecular weight of 400 or less, more preferably a molecular weight of 300 or less, still more preferably a molecular weight of 200 or less, and most preferably a molecular weight of 100 or less.

In preferred embodiments, the at least one Lewis basic donor ligand is selected from ligands containing a donor atom selected from oxygen, sulphur, nitrogen and phosphorus, more preferably from oxygen, sulphur and phosphorus, still more preferably from oxygen and sulphur. Most preferably, the at least one Lewis basic donor ligand is selected from ligands containing an oxygen donor atom.

In further preferred embodiments, the at least one Lewis basic donor ligand is selected from the group of compounds consisting of ketones, sulfoxides, phosphine-oxides, ureas, esters, amides, ethers, thioketones, thioureas, thioamides, thioethers, amines, nitriles and phosphines. More preferably, the at least one Lewis basic donor ligand is selected from the group of compounds consisting of ketones, sulfoxides, phosphine-oxides, ureas, esters, amides, ethers, thioketones, thioureas, thioamides and thioethers. Still more preferably, the at least one Lewis basic donor ligand is selected from the group of compounds consisting of ketones, sulfoxides, phosphine oxides, ureas, esters, amides and ethers. Still more preferably, the at least one Lewis basic donor ligand is selected from the group of compounds consisting of sulfoxides, ureas and amides. Most preferably, the at least one Lewis basic donor ligand is an amide or a urea ligand.

In further preferred embodiments, the at least one Lewis basic donor ligand is selected from compounds having a formula selected from $R^1$—C(O)—$R^1$, $R^1$—S(O)—$R^1$, $R^2NH$—C(O)—$NHR^2$, $R^2NH$—C(S)—$NHR^2$, $R^1$—C(O)—$NR^2_2$, $R^1$—C(O)—$OR^1$, $(R^3)_3P(O)$ and $R^1$—CN wherein:

each $R^1$ independently represents a $C_1$ to $C_{10}$ straight chain or branched alkyl group, preferably a $C_1$ to $C_6$ alkyl group, more preferably a $C_1$ to $C_3$ alkyl group and most preferably a methyl group;

$R^2$ is selected from hydrogen or a $C_1$ to $C_{10}$ straight chain or branched alkyl group, more preferably from hydrogen or a $C_1$ to $C_6$ alkyl group, still more preferably from hydrogen or a $C_1$ to $C_3$ alkyl group, and most preferably from hydrogen or a methyl group; and $R^3$ represents a $C_4$ to $C_{10}$ straight chain or branched alkyl group, wherein any of $R^1$, $R^2$ and $R^3$ may optionally be substituted by one or more fluorine atoms.

Examples of suitable $C_1$ to $C_{10}$ alkyl groups include methyl, ethyl, propyl, isopropyl, n-butyl, iso-butyl, sec-butyl, tert-butyl, n-pentyl, n-hexyl, n-heptyl, n-octyl, n-nonyl, n-decyl, trifluoromethyl and pentafluoroethyl. Preferred alkyl groups include methyl, ethyl, propyl, isopropyl, n-butyl, iso-butyl, sec-butyl, tert-butyl, n-pentyl, and n-hexyl. More preferred alkyl groups include methyl, ethyl, propyl, and isopropyl. Most preferably, the alkyl group is methyl.

In still further preferred embodiments, the at least one Lewis basic donor ligand is selected from compounds having a formula selected from $R^1$—S(O)—$R^1$, $R^2NH$—C(O)—$NHR^2$, $R^2NH$—C(S)—$NHR^2$, $R^1$—C(O)—$NR^2_2$ and $(R^3)_3P(O)$; more preferably, the at least one Lewis basic donor ligand is selected from compounds having a formula selected from $R^2NH$—C(O)—$NHR^2$ and $R^1$—C(O)—$NR^2_2$; and most preferably the at least one Lewis basic donor ligand is a compound having the formula $R^2NH$—C(O)—$NHR^2$, wherein $R^1$ and $R^2$ are as defined above.

Examples of suitable Lewis basic donor ligands in accordance with the present invention include urea, N,N'-dimethylurea, N,N'-dimethylthiourea, acetamide, dimethylacetamide, acetone, ethyl acetate dimethylsulfoxide and trioctylphosphine oxide. More preferably, the at least one Lewis basic donor ligand is selected from urea and acetamide. Most preferably, the at least one Lewis basic donor ligand is urea.

In some embodiments of the invention, the at least one Lewis basic donor ligand may comprise a mixture of two or more Lewis basic donor ligands as described herein.

Preferred liquid complex catalysts in accordance with the present invention comprise $AlCl_3$ and a ligand selected from urea, N,N'-dimethylurea, N,N'-dimethylthiourea, acetamide, and dimethylacetamide in a molar ratio of $AlCl_3$ to ligand of from 1:1 ($\chi_{AlCl3}$=0.50) to 2:1 ($\chi_{AlCl3}$=0.67), preferably in a molar ratio of $AlCl_3$ to ligand of from 55:45 ($\chi_{MX3}$=0.55) to about 65:35 ($\chi_{MX3}$=0.65), and more preferably in a molar ratio of $AlCl_3$ to ligand of about 3:2 ($\chi_{AlCl3}$=0.60). More preferably the liquid complex catalyst comprises $AlCl_3$ and urea in a molar ratio of about 3:2, or the liquid complex catalyst comprises $AlCl_3$ and acetamide in a molar ratio of about 3:2. Most preferably, the liquid complex catalyst comprises $AlCl_3$ and urea in a molar ratio of about 3:2.

As used herein, the term "olefinic feedstock comprising $C_5$ to $C_{20}$ alpha-olefins" preferably refers to a hydrocarbonaceous feedstock that comprises at least one $C_5$ to $C_{20}$ alpha-olefin hydrocarbon. Preferably, the olefinic feedstock comprises at least 50 wt % of one or more $C_5$ to $C_{20}$ alpha-olefins, more preferably at least 60 wt % of one or more $C_5$ to $C_{20}$ alpha-olefins, more preferably at least 70 wt % of one or more $C_5$ to $C_{20}$ alpha-olefins, more preferably at least 80 wt % of one or more $C_5$ to $C_{20}$ alpha-olefins, more preferably at least 90 wt % of one or more $C_5$ to $C_{20}$ alpha-olefins, and most preferably at least 95 wt % of one or more $C_5$ to $C_{20}$ alpha-olefins. In some embodiments, the olefinic feedstock may comprise at least 98 wt % of one or more $C_5$ to $C_{20}$ alpha-olefins, or at least 99 wt % of one or more $C_5$ to $C_{20}$ alpha-olefins. The remainder of the olefinic feedstock may suitably be composed of other olefins, paraffins, or a mixture thereof.

In preferred embodiments, the olefinic feedstock comprises at least 50 wt % $C_6$ to $C_{18}$ alpha-olefins, more preferably at least 60 wt % $C_6$ to $C_{18}$ alpha-olefins, more preferably at least 70 wt % $C_6$ to $C_{18}$ alpha-olefins, still more preferably at least 80 wt % $C_6$ to $C_{18}$ alpha-olefins, and most preferably at least 90 wt % $C_6$ to $C_{18}$ alpha-olefins. For example, the olefinic feedstock may comprise at least 95 wt % $C_6$ to $C_{18}$ alpha-olefins, at least 98 wt % $C_6$ to $C_{18}$ alpha-olefins or at least 99 wt % $C_6$ to $C_{18}$ alpha-olefins.

In some embodiments, the olefinic feedstock comprises at least 30 wt % $C_8$ to $C_{14}$ alpha-olefins, more preferably at least 50 wt % $C_8$ to $C_{14}$ alpha-olefins, more preferably at least 70 wt % $C_8$ to $C_{14}$ alpha-olefins, still more preferably at least 80 wt % $C_8$ to $C_{14}$ alpha-olefins, and most preferably at least 90 wt % $C_8$ to $C_{14}$ alpha-olefins. For example, the olefinic feedstock may comprise at least 95 wt % $C_8$ to $C_{14}$ alpha-olefins, at least 98 wt % $C_8$ to $C_{14}$ alpha-olefins or at least 99 wt % $C_8$ to $C_{14}$ alpha-olefins.

In more preferred embodiments, the olefinic feedstock comprises at least 30 wt % $C_{10}$ to $C_{12}$ alpha-olefins, more preferably at least 50 wt % $C_{10}$ to $C_{12}$ alpha-olefins, more preferably at least 70 wt % $C_{10}$ to $C_{12}$ alpha-olefins, still more preferably at least 80 wt % $C_{10}$ to $C_{12}$ alpha-olefins, and most preferably at least 90 wt % $C_{10}$ to $C_{12}$ alpha-olefins. For example, the olefinic feedstock may comprise at least 95 wt % $C_{10}$ to $C_{12}$ alpha-olefins, at least 98 wt % $C_{10}$ to $C_{12}$ alpha-olefins or at least 99 wt % $C_{10}$ to $C_{12}$ alpha-olefins.

In some embodiments, the olefinic feedstock preferably comprises at least 30 wt % 1-decene, more preferably at least 50 wt % 1-decene, more preferably at least 70 wt % 1-decene, still more preferably at least 80 wt % 1-decene, and most preferably at least 90 wt % 1-decene. For example, the olefinic feedstock may comprise at least 95 wt % 1-decene, at least 98 wt % 1-decene or at least 99 wt % 1-decene.

In other embodiments, the olefinic feedstock preferably comprises at least 30 wt % 1-dodecene, more preferably at least 50 wt % 1-dodecene, more preferably at least 70 wt % 1-dodecene, still more preferably at least 80 wt % 1-dodecene and most preferably at least 90 wt % 1-dodecene. For example, the olefinic feedstock may comprise at least 95 wt % 1-dodecene, at least 98 wt % 1-dodecene or at least 99 wt % 1-dodecene.

In further embodiments, the olefinic feedstock may comprise at least 30 wt % $C_{16}$ to $C_{18}$ alpha-olefins, more preferably at least 50 wt % $C_{16}$ to $C_{18}$ alpha-olefins, more preferably at least 70 wt % $C_{16}$ to $C_{18}$ alpha-olefins, still more preferably at least 80 wt % $C_{16}$ to $C_{18}$ alpha-olefins, and most preferably at least 90 wt % $C_{16}$ to $C_{18}$ alpha-olefins. For example, the olefinic feedstock may comprise at least 95 wt % $C_{16}$ to $C_{18}$ alpha-olefins, at least 98 wt % $C_{16}$ to $C_{18}$ alpha-olefins or at least 99 wt % $C_{16}$ to $C_{18}$ alpha-olefins.

In some embodiments, the olefinic feedstock preferably comprises at least 30 wt % 1-hexadecene, more preferably at least 50 wt % 1-hexadecene, more preferably at least 70 wt % 1-hexadecene, still more preferably at least 80 wt % 1-hexadecene, and most preferably at least 90 wt % 1-hexadecene. For example, the olefinic feedstock may comprise at least 95 wt % 1-hexadecene, at least 98 wt % 1-hexadecene or at least 99 wt % 1-hexadecene.

In other embodiments, the olefinic feedstock preferably comprises at least 30 wt % 1-octadecene, more preferably at least 50 wt % 1-octadecene, more preferably at least 70 wt % 1-octadecene, still more preferably at least 80 wt % 1-octadecene and most preferably at least 90 wt % 1-octadecene. For example, the olefinic feedstock may comprise at least 95 wt % 1-octadecene, at least 98 wt % 1-octadecene or at least 99 wt % 1-octadecene.

In some embodiments of the invention, the olefinic feedstock may also comprise paraffins. In general, the olefinic feedstock comprises a minor amount of paraffins. For instance, the olefinic feedstock may optionally comprise up to 20 wt % paraffins, for instance up to 10 wt % paraffins, or up to 5 wt % paraffins. However, it will be appreciated that olefinic feedstocks comprising larger amounts of paraffins are also suitable as feedstocks for the present invention. For instance, olefinic feedstocks comprising up to 60 wt %, 70 wt %, 80 wt % or 90 wt % paraffins are found to be suitable feedstocks for the process of the present invention. The presence of a minor amount of paraffins in the olefinic feedstock is observed to suppress the formation of undesired heavy oligomers. Suitable paraffins include $C_5$ to $C_{20}$ paraffins, such as $C_{10}$ to $C_{12}$ paraffins.

The olefinic feedstock may suitably be contacted with the liquid complex catalyst at a temperature of from 0° C. up to the boiling point of the alpha-olefins at the reaction pressure. Preferably, the olefinic feedstock is contacted with the liquid complex catalyst at a temperature of from 0 to 160° C., more preferably 40 to 140° C., more preferably 80 to 140° C., still more preferably 100 to 140° C., and most preferably about 120° C. The formation of oligomers in accordance with the present invention is exothermic, and thus a cooling system may be used so as to maintain the desired reaction temperature.

The olefinic feedstock may suitably be contacted with the liquid complex catalyst at a pressure of from 10 to 1000 kPa, preferably from 20 to 500 kPa, more preferably from 50 to 200 kPa, for instance from 80 to 120 kPa. Preferably, the olefinic feedstock is contacted with the liquid complex catalyst at ambient pressure, i.e. around 100 kPa.

The olefinic feedstock may suitably be contacted with the liquid complex catalyst for a period of from 1 minute to 10 hours, for example from 10 minutes to 1 hour.

The reaction is preferably carried out under an inert atmosphere and substantially in the absence of moisture, defined as less than 800 ppm by weight water based on the total weight of liquid complex catalyst and olefinic feedstock.

The process of the present invention may suitably be carried out by contacting the olefinic feedstock with at least 0.01 wt % of the liquid complex catalyst, more preferably at least 0.05 wt % of the liquid complex catalyst, still more preferably at least 0.1 wt % of the liquid complex catalyst, and most preferably at least 0.2 wt % of the liquid complex catalyst, based on the total weight of the liquid complex catalyst and olefinic feedstock. For example, the olefinic feedstock may suitably be contacted with from 0.01 to 5 wt % of the liquid complex catalyst, preferably from 0.05 to 2 wt % of the liquid complex catalyst, still more preferably from 0.1 to 1 wt % of the liquid complex catalyst, and still more preferably from 0.2 to 0.8 wt % of the liquid complex catalyst, based on the total weight of the liquid complex catalyst and olefinic feedstock. Most preferably, the olefinic feedstock is contacted with about 0.5 wt % of the liquid complex catalyst, based on the total weight of the liquid complex catalyst and olefinic feedstock.

It has been found that the oligomerised product distribution is not dependent on the catalyst loading to any significant degree. However, higher catalyst loadings generally reduce the reaction time and improve conversion of starting materials. Due to the exothermic nature of the reaction, the use of higher catalyst loadings may in some cases necessitate additional measures to maintain the desired reaction temperature.

The oligomer product obtained by the present invention may be separated from the liquid complex catalyst by any suitable means, for instance by gravity separation and decantation or by centrifugation. Alternatively, the reaction may be quenched by the addition of water, optionally containing a mild base, and the organic and aqueous phases may be separated, for instance by gravity separation and decantation or by centrifugation.

The oligomerised product obtained by the process of the present invention typically contains minor amounts of highly oligomerised products (defined herein as hexamers and higher oligomers) as well as unreacted starting material. In some embodiments, the process of the invention may further comprise distillation of the oligomerised product to separate starting material and/or highly oligomerised products from the desired lower oligomers (defined herein as dimers, trimers, tetramers and pentamers).

The catalytic oligomerisation of alpha-olefins generally provides oligomerised products that contain one remaining double bond. The presence of double bonds generally reduces the oxidative stability of a lubricating oil base stock. Thus, in some embodiments, the process of the present invention further comprises a step in which the remaining olefinic double bonds in the oligomerised product are reduced to carbon-carbon single bonds so as to improve the oxidation stability of the product. Suitably, the reduction of olefinic double bonds may be carried out by hydrogenation in the presence of a suitable hydrogenation catalyst, for instance a Group VIII metal such as platinum, palladium, nickel, rhodium or iridium on a solid support. In other embodiments, the process may further comprise a step in which the remaining olefinic double bonds in the oligomerised product are alkylated.

In preferred embodiments, the process of the present invention is selective for the preparation of dimers, trimers and tetramers. In further preferred embodiments, the process of the present invention is selective for the preparation of dimers and trimers. As noted above, the formation of higher oligomers may be suppressed, if required, by the inclusion of paraffins in the olefinic feedstock.

The oligomerised products produced according to the process of the present invention have a range of desirable properties.

In some embodiments, the oligomerised products produced according to the process of the present invention have a Kv40 of from 5 to 60 cSt, preferably from 10 to 40 cSt.

In some embodiments, the oligomerised products produced according to the process of the present invention have a Kv100 of from 1 to 15 cSt, preferably from 1.5 to 10 cSt, more preferably from 1.5 to 8.5 cSt (such as 2, 4, 6 or 8), still more preferably from 3.5 to 8.5 cSt (such as 4, 6 or 8), and most preferably from 3.5 to 6.5 cSt (such as 4 or 6).

In some embodiments, the oligomerised products produced according to the process of the present invention have a pour point of $-20°$ C. or less, preferably of $-30°$ C. or less (in accordance with ASTM D97-11).

In some embodiments, the oligomerised products produced according to the process of the present invention have a viscosity index (VI) of 100 or greater, more preferably from 120 to 160 (according to ASTM D2270).

The present invention will now be illustrated by reference to the following Examples and the accompanying figures, in which.

EXAMPLES

Reference Example 1—Synthesis of $[C_2mim][Al_2Cl_7]$

Figure 1:
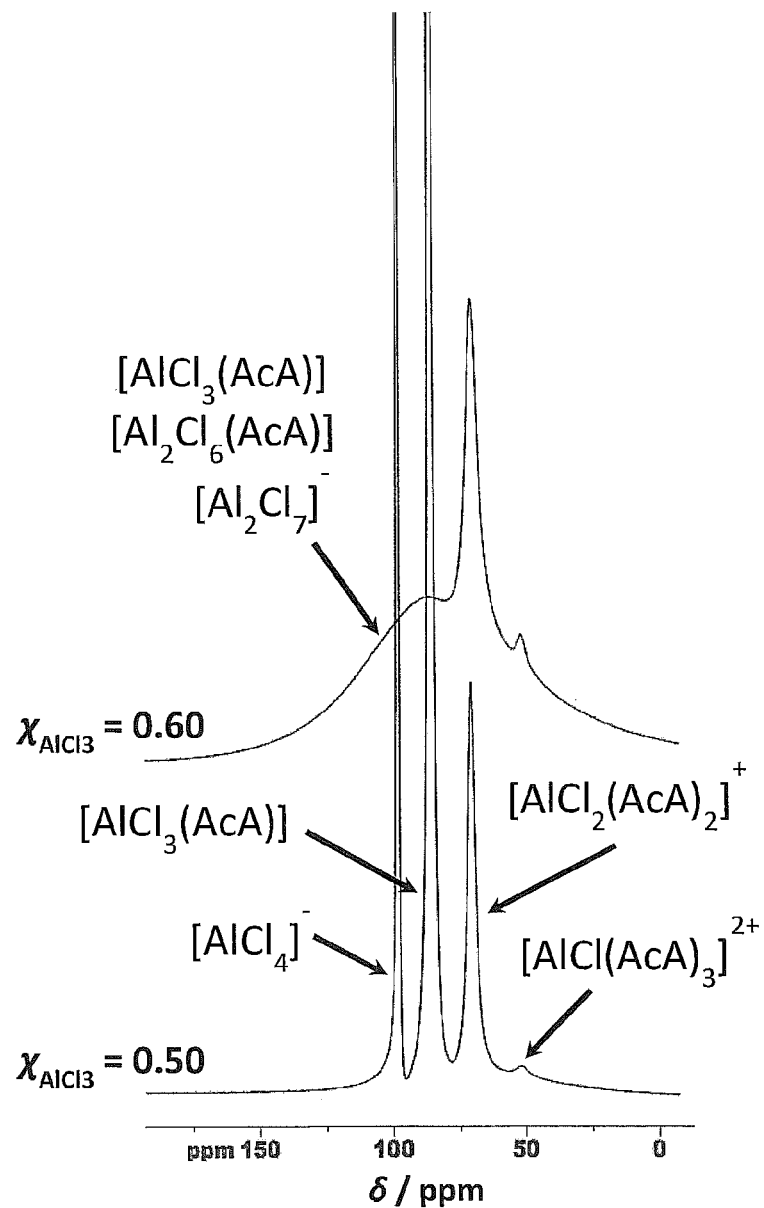
FIG. 1 shows the overlaid $^{27}$Al NMR spectra for LC compositions obtained from AlCl$_3$ and acetamide (AcA) where $\chi_{AlCl3}$ is 0.50 and 0.60.

The ionic liquid 1-ethyl-3-methylimidazolium chloride-$AlCl_3$ with $\chi_{AlCl3}$=0.67 (referred to herein as $[C_2mim][Al_2Cl_7]$) was prepared by slowly adding of aluminium (III) chloride (33.60 g, 0.252 mol) to $[C_2mim]Cl$ (18.46 g, 0.126 mol) under an inert atmosphere. A clear, light brown, mobile ionic liquid was generated in the course of an exothermic reaction.

Example 2—Synthesis of $AlCl_3$-Urea Liquid Complexes

LCs having $\chi_{AlCl3}$ values of from 0.5 to 0.67 were prepared from aluminium (III) chloride and urea by slowly adding 1 molar equivalent of urea to 1 to 2 molar equivalents of aluminium (III) chloride with stirring under an inert atmosphere. Once addition of the urea ligand was complete, the resulting mixture was stirred at 80° C. for 1 hour to provide a homogeneous, mobile, colourless liquid. The LCs were stored under an inert atmosphere until used.

Example 3—Synthesis of Other Liquid Complexes

LCs containing ligands selected from dimethylacetamide, trioctylphosphine oxide, dimethyl sulfoxide, ethyl acetate, N,N'-dimethylthiourea, acetone and acetonitrile and each having $\chi_{AlCl3}$=0.60 were prepared by an analogous procedure to Example 2, using 3 molar equivalents of aluminium (III) chloride and two molar equivalents of the ligand. The properties of the different liquid complexes are described in Table 1.

TABLE 1

| Ligand | Result |
| --- | --- |
| Dimethylacetamide | Colourless, mobile liquid |
| Trioctylphosphine oxide | Yellow, slightly viscous liquid |
| Dimethyl sulfoxide | Dark brown, mobile liquid |
| Ethyl acetate, | Yellow, mobile liquid |
| N,N'-dimethylthiourea | Colourless, mobile liquid |
| Acetone | Yellow, mobile liquid |
| Acetonitrile | Room temperature solid, melting point ca. 80° C. |

Example 4—Generic Procedure for Oligomerisation Reactions

Oligomerisation reactions were conducted in a battery of computer-controlled reactors, each having a volume of 120 mL. Due to the corrosive nature of the catalyst, the reactors are designed for high corrosion resistance, with the sample remaining in contact only with glass, Teflon™ and Haste-Hoy™. Prior to the reaction, the reactor vessels and stirrer propellers are dried overnight in an oven, and subsequently cooled to ambient temperature in a desiccator containing phosphorus(V) oxide. The remaining parts are dried with a heat gun immediately before assembly.

1-Decene (40 mL, dry by Karl-Fisher analysis) is added to each reactor vessel and the reactors are purged with dry argon. The reactors are then equilibrated to the required reaction temperature with vigorous stirring (600 rpm).

Immediately prior to use, the liquid complex or ionic liquid is loaded into a gas-tight syringe in a glovebox. Prior to use, the syringe is dried overnight in an oven, cooled in a desiccator and then transferred directly to the glovebox. The tip of the needle is plunged into a small flask closed with a septum to protect it from contact with the atmosphere. Subsequently, the loaded syringe is removed from the glovebox and the needle is immediately plunged through a septum into a reactor containing the 1-decene feedstock at the required reaction temperature and stirred at 600 rpm.

The liquid complex or ionic liquid catalyst is added drop-wise to the vigorously stirred feedstock as quickly as possible, but maintaining a substantially constant reaction temperature (i.e. avoiding exotherms greater than 10° C.). After stirring at the required reaction temperature for the specified reaction time, the reaction mixture is quenched by vigorous stirring (600 rpm, 10 min, ambient temperature) with deionised water (30 mL). Aqueous ammonia (10%, 10 mL) added and the mixture is subsequently centrifuged to fully partition the aqueous and organic phases.

The boiling point distribution of oligomerised products was generated by simulated distillation (SimDist) according to ASTM 6352. Simulated distillation is a technique widely used in the petroleum industry for evaluation of hydrocarbon products in which the boiling point distribution of a mixture of hydrocarbons is calibrated to the gas chromatographic analysis of the mixture. Samples of SimDist analysis were dissolved in toluene (100 mg·cm$^{-3}$), dried over magnesium sulphate and filtered prior to analysis. SimDist analyses are shown as cumulative distributions with the maximum molecular weight of the oligomers suitable for use as lubricant base stocks indicated by a horizontal line at a boiling point of ca. 580° C. Highly oligomerised products having a boiling point above 580° C. are referred to herein as "heavies".

Pour points were measured in accordance with ASTM D97-11 or by a simulation thereof using a series of ice salt and dry ice-solvent baths from 0° C. down to −51° C.

Kinematic viscosity (Kv) is measured at 40° C. and 100° C. using the appropriate Cannon-Fenske kinematic viscosity glassware and a dedicated, precisely-controlled heating bath. Kinematic viscosity is found by timing the gravitational flow of the sample through a capillary, with temperature maintained using a high accuracy heating bath.

In order to select appropriate Cannon-Fenske tubes, dynamic viscosity of some samples was measured using Bohlin Gemini cone-and-plate viscometer with a Bohlin Instruments Peltier temperature control and a stainless steel 4/40 spindle. Dynamic viscosity was measured within a temperature range of 20-95° C., in 5° C. increments. From dynamic viscosity ($\mu$) and density ($\rho$) kinematic viscosity, Kv was estimated using the following relationship: Kv≈$\mu\rho$−1, to select the appropriate Cannon-Fenske tubes.

Viscosity Index (VI) was calculated from the measured Kv40 and Kv100 values according to ASTM D2270.

Reference Example 5—Oligomerisation of 1-Decene Using [C$_2$mim]Cl—AlCl$_3$($\chi_{AlCl3}$=0.55)

Figure 2:
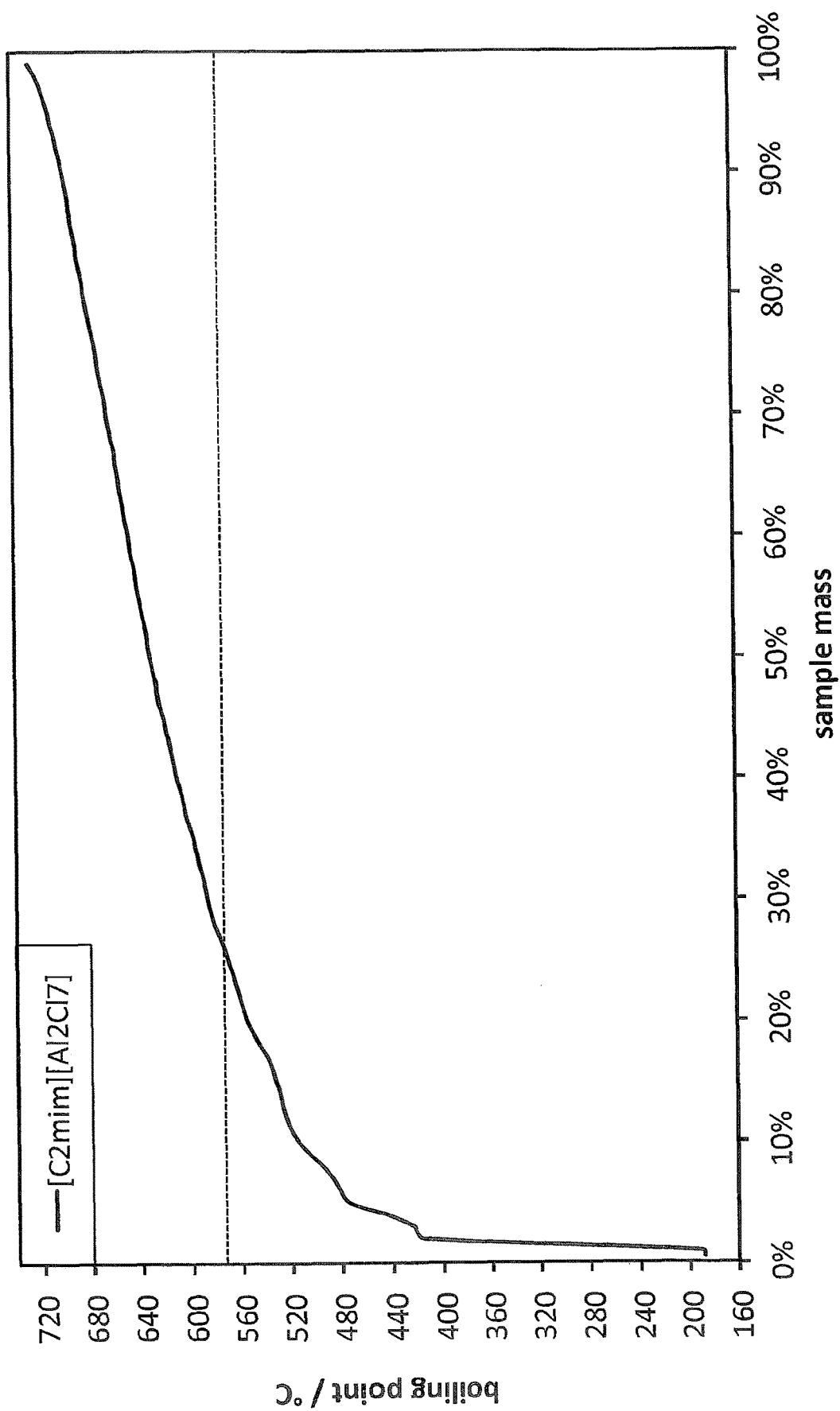
FIG. 2 shows the simulated distillation (SimDist) analysis of the product distribution obtained by oligomerising 1-decene in the presence of [C$_2$mim][Al$_2$Cl$_7$] (i.e. [C$_2$mim]Cl—AlCl$_3$, $\chi_{AlCl3}$=0.67).

Oligomerisation of 1-decene was carried out in the presence of 1.5 wt % of the ionic liquid of Reference Example 1 according to the general procedure of Example 4 with a reaction temperature of 120° C. and a reaction time of 20 minutes. The results of the SimDist analysis are provided in FIG. 2. While the conversion of starting materials is found to be very high, the oligomeric product obtained using this ionic liquid contains a large proportion of highly oligomerised products, with approximately 80 wt % of the products in the heavies range.

Example 6—Oligomerisation of 1-Decene Using LC Catalyst

Oligomerisation of 1-decene was carried out according to the general procedure of Example 4 in the presence of a LC catalyst prepared from AlCl$_3$ and urea (Ur), ($\chi_{AlCl3}$=0.60). The reaction was carried out at 120° C. for a period of 20 minutes using 1.85 wt % of the LC catalyst.

Figure 3:
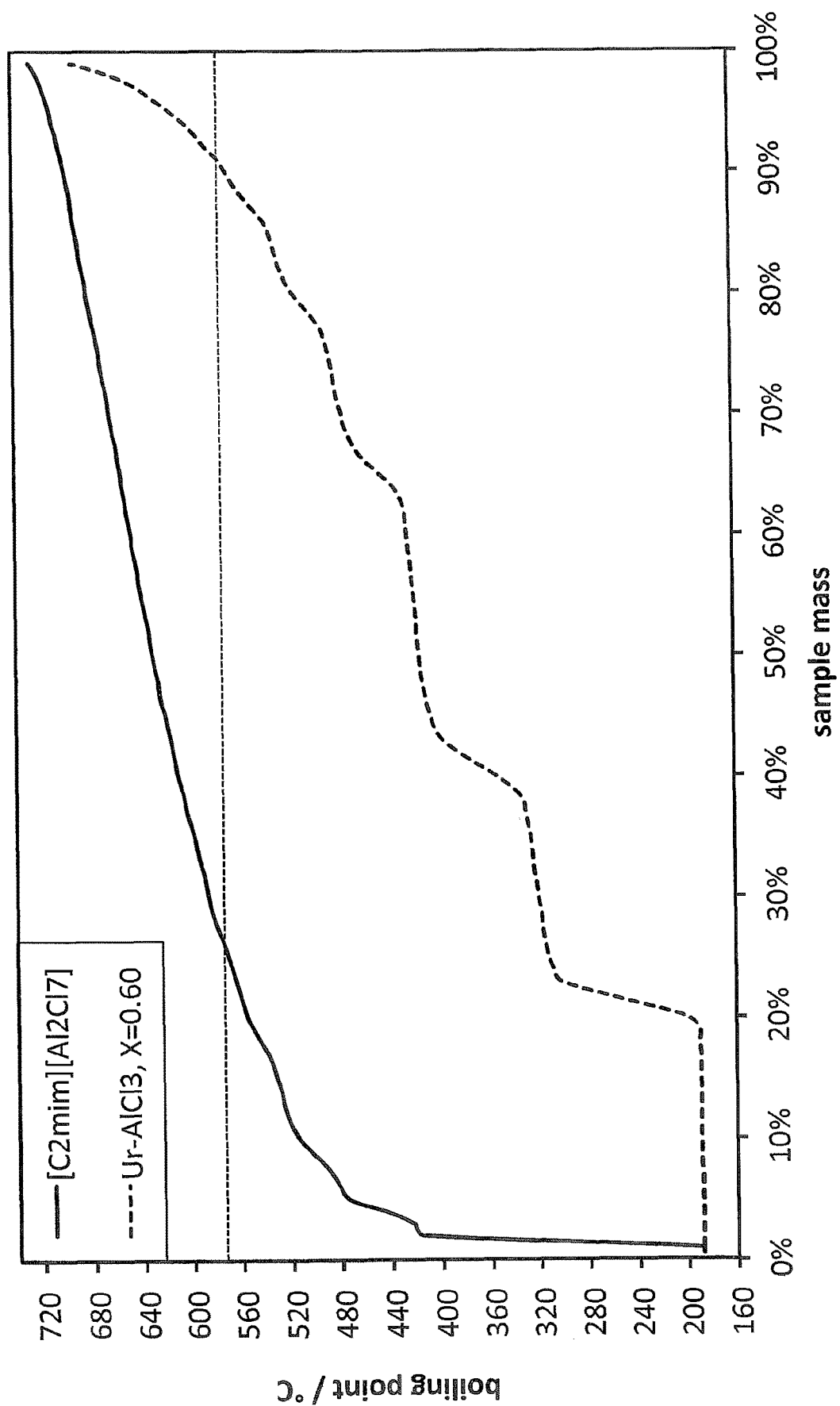
FIG. 3 shows the SimDist analysis of the product distribution obtained by oligomerising 1-decene in the presence of a LC prepared from AlCl$_3$ and urea (Ur) ($\chi_{AlCl3}$=0.60). The product distribution obtained using [C$_2$mim][Al$_2$Cl$_7$] is also shown for reference.

The SimDist results are provided in FIG. 3 (the results for Reference Example 5 are also shown in FIG. 3 for reference). It is found that the LC system of the present invention provides oligomerised products with conversions of starting material as high as 85 wt % and with far lower production of heavies than the ionic liquid system of Reference Example 5. Numerical results are also provided in Table 2 below (see Example 7).

Example 7—Oligomerisation of 1-Decene Using LC Catalysts

Oligomerisation of 1-decene was carried out according to the general procedure of Example 4 in the presence of LC catalysts prepared from AlCl$_3$ and a ligand selected from trioctylphosphine oxide (P$_{888}$O), dimethylthiourea (SUr), acetone (Act), ethyl acetate (EtOAc), dimethylsulfoxide (DMSO) and dimethylacetamide (DMA) with $\chi_{AlCl3}$=0.60 in each case. The reactions were carried out at 120° C. for a period of 20 minutes using 1 mol % (ca. 1.8 wt %) of the LC catalyst.

Figure 4:
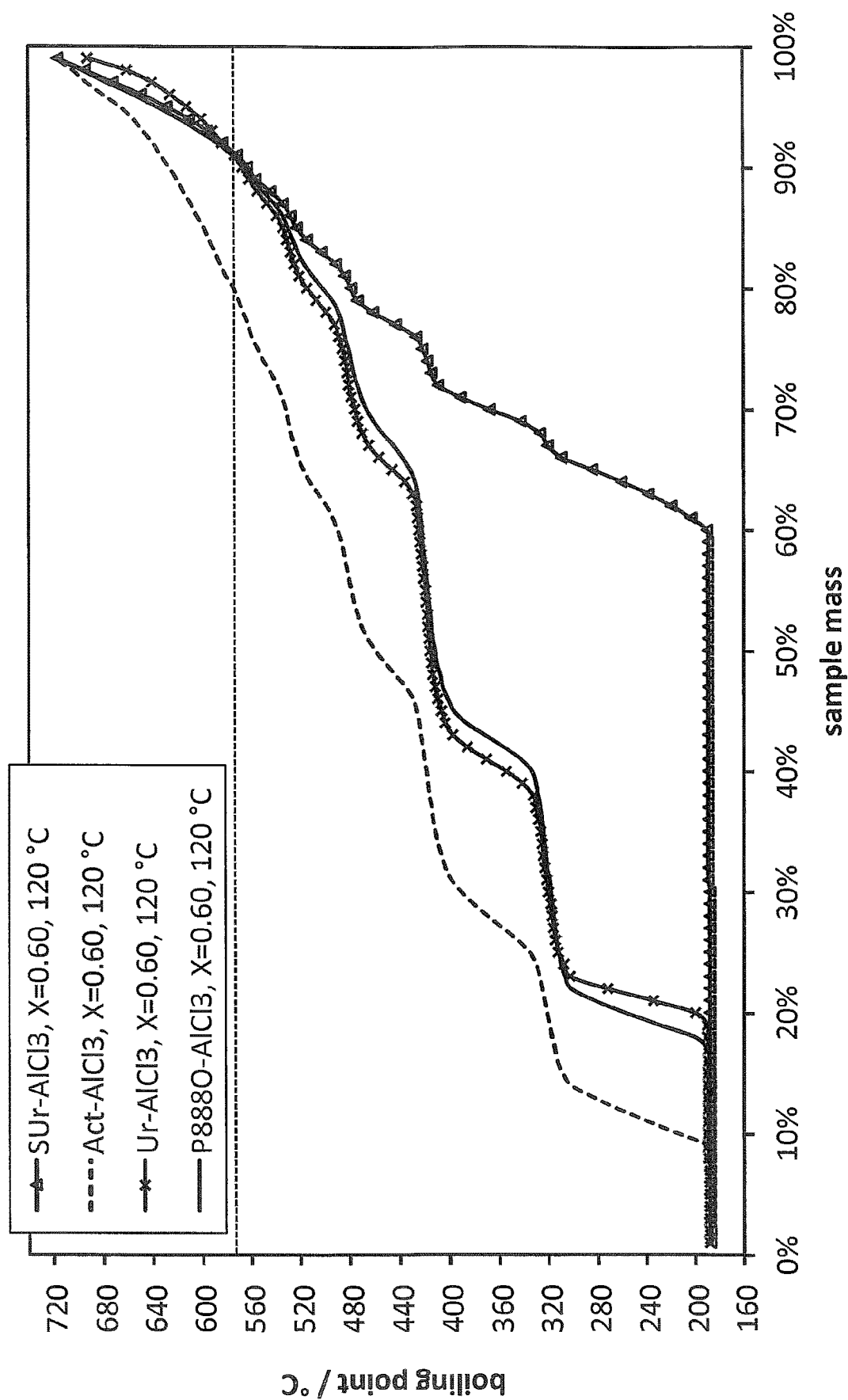
FIG. 4 shows the SimDist analyses of the product distributions obtained by oligomerising 1-decene in the presence of LCs prepared from AlCl$_3$ and a ligand selected from urea (Ur), trioctylphosphine oxide (P$_{888}$O), dimethylthiourea (SUr), and acetone (Act) ($\chi_{AlCl3}$=0.60 in each case).
Figure 5:
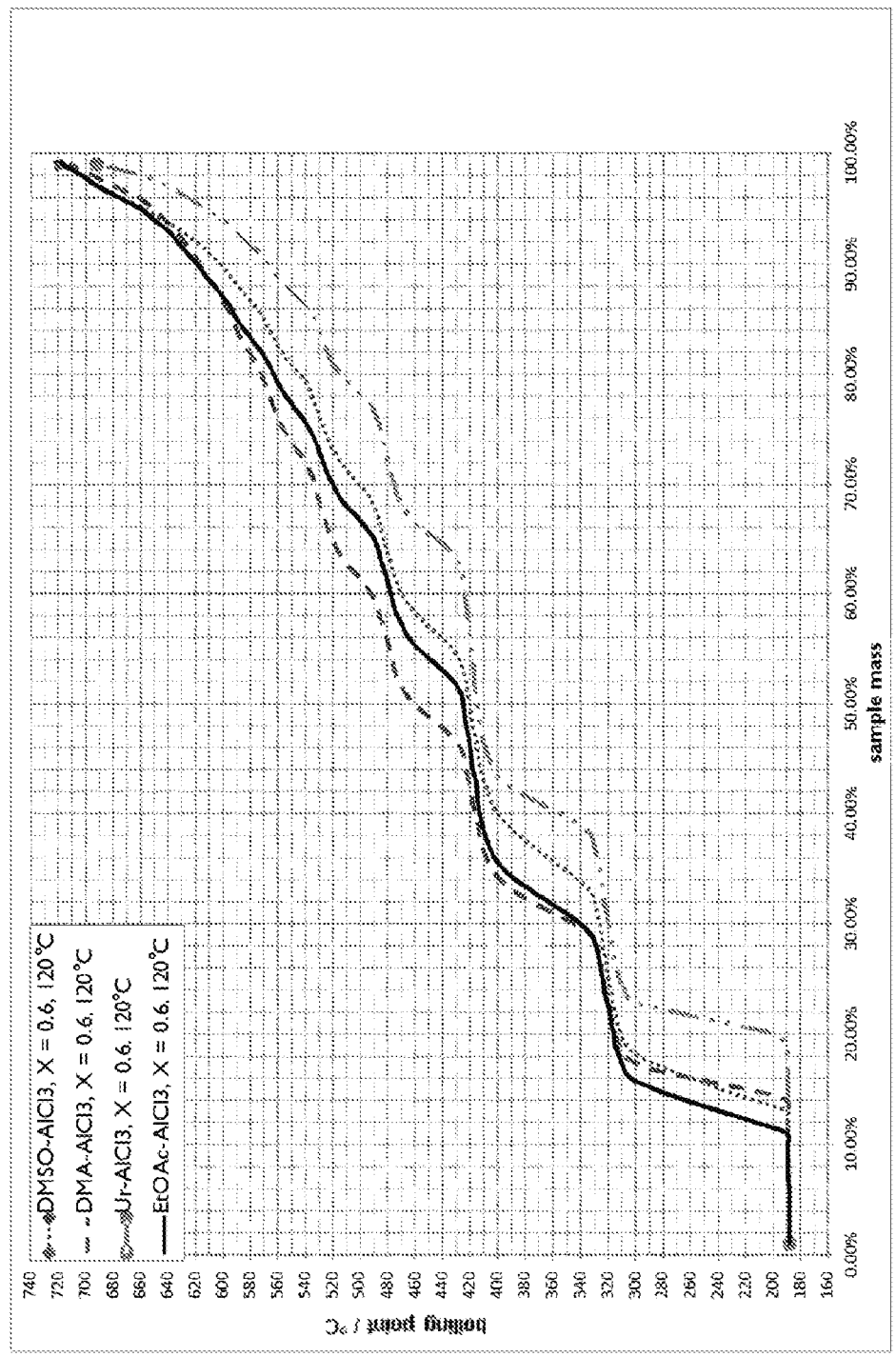
FIG. 5 shows the SimDist analyses of the product distributions obtained by oligomerising 1-decene in the presence of LCs prepared from AlCl$_3$ and a ligand selected from urea (Ur), ethyl acetate (EtOAc), dimethylsulfoxide (DMSO) and dimethylacetamide (DMA) ($\chi_{AlCl3}$=0.60 in each case).

The SimDist results are provided in FIGS. 4 and 5 (the results for urea are shown in both Figures for reference). It is found that the LC systems of the present invention provide oligomerised products with conversions of starting material as high as 85 wt % and with far lower production of heavies than the ionic liquid system of Reference Example 5. Numerical results are also provided in Table 2.

TABLE 2

| Ligand | Conversion mass % | C20 | C30 | C40 | C50 | C60 | C70+ |
|---|---|---|---|---|---|---|---|
| | | | mass % of product | | | | |
| Ur | 71.0 | 47.1 | 38.6 | 11.4 | 2.9 | — | — |
| DMSO | 82.0 | 28.4 | 32.1 | 23.5 | 11.1 | 4.9 | — |
| EtOAc | 82.0 | 27.2 | 33.3 | 21.0 | 9.9 | 6.2 | 2.5 |
| Act | 85.0 | 21.4 | 32.1 | 22.6 | 13.1 | 6.0 | 4.8 |
| SUr | 22.0 | 14.3 | 33.3 | 28.6 | 19.0 | 4.8 | — |
| P$_{888}$O | 74.0 | 35.6 | 43.8 | 16.4 | 4.1 | — | — |
| DMA | 80.0 | 27.8 | 29.1 | 21.5 | 12.7 | 6.3 | 2.5 |

Example 8—Oligomerisation of 1-Decene Using Further LC Catalysts

Figure 6:
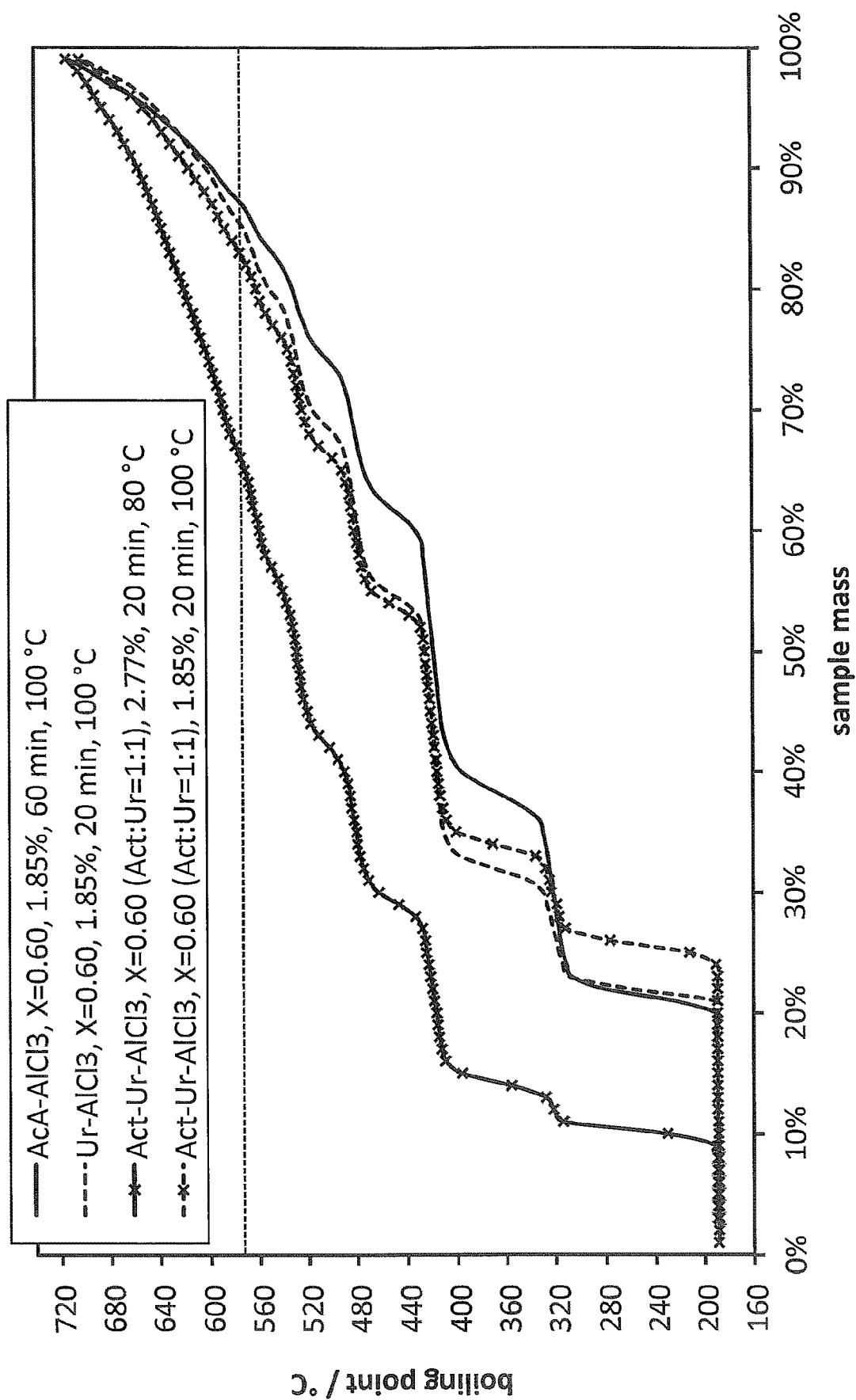
FIG. 6 shows the SimDist analyses of the product distributions obtained by oligomerising 1-decene in the presence of LCs prepared from AlCl$_3$ and a ligand selected from acetamide (AcA), urea, a 1:1 binary mixture of acetone and urea, and a 1:1 binary mixture of acetamide and urea, ($\chi_{AlCl3}$=0.60 in each case).

Oligomerisation of 1-decene was carried out according to the general procedure of Example 4 in the presence of further LC catalysts prepared from AlCl$_3$ and a ligand selected from acetamide (AcA), urea, a 1:1 binary mixture of acetone and urea, and a 1:1 binary mixture of acetamide and urea, with $\chi_{AlCl3}$=0.60 in each case. The reaction times were 1 hour for the LC containing only acetamide as a ligand and 20 minutes in all other cases. The reaction temperature was 80° C. for the LC containing a 1:1 mixture of acetone and urea, and the catalyst loading was 2.77 wt %. In all other cases a temperature of 100° C. and a catalyst loading of 1.85 wt % was used. The SimDist results are provided in FIG. 6. The result obtained at 80° C. indicates that lower temperatures provide a greater proportion of heavy oligomers.

Example 9—Temperature Dependence of LC Catalysed Oligomerisation of 1-Decene

Figure 7:
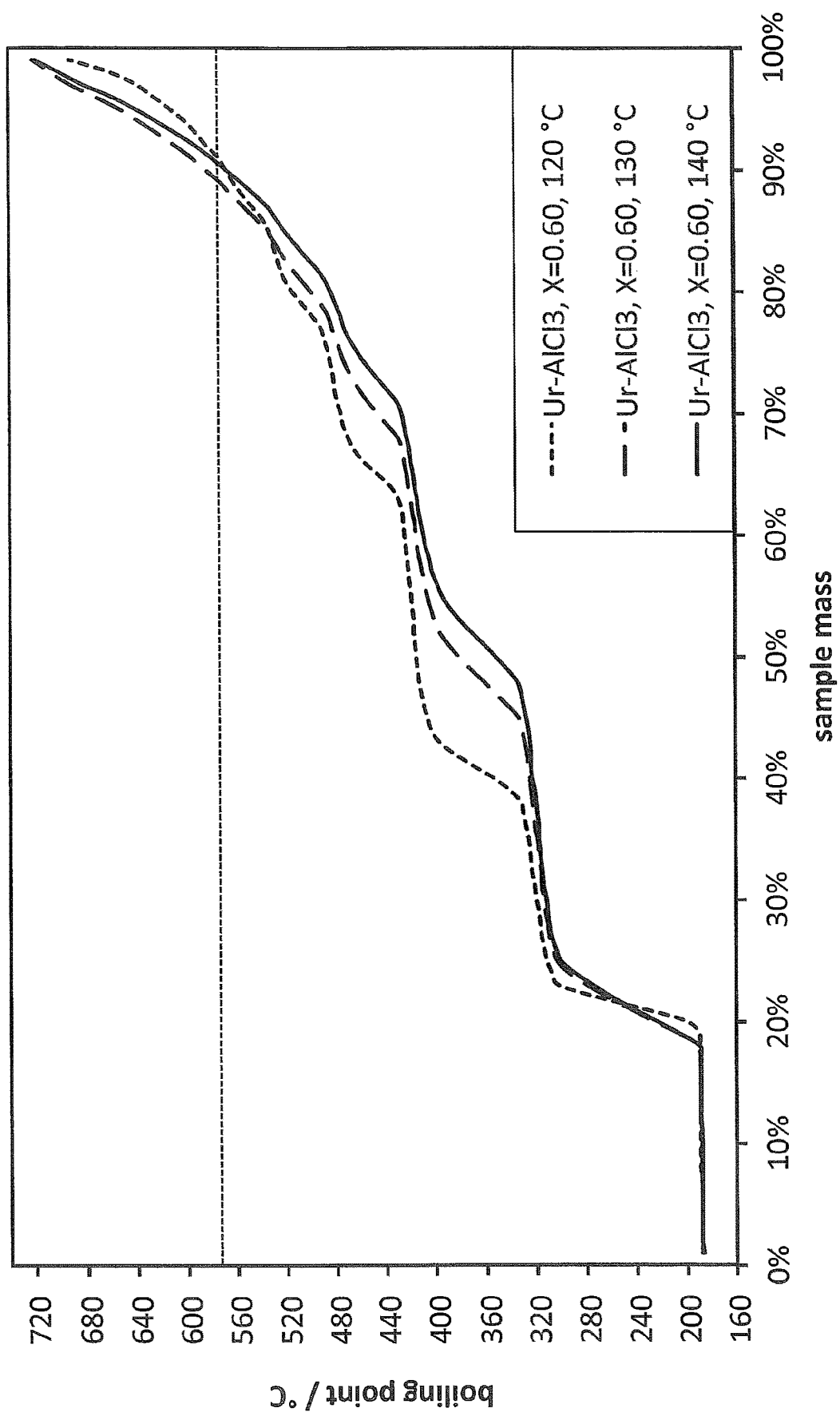
FIG. 7 shows the SimDist analyses of the product distributions obtained by oligomerising 1-decene in the presence of a LC prepared from AlCl$_3$ and urea ($\chi_{AlCl3}$=0.60) at a range of temperatures.

Oligomerisation of 1-decene was carried out according to the general procedure of Example 4 in the presence of 1.85 wt % of a LC catalyst prepared from AlCl$_3$ and urea ($\chi_{AlCl3}$=0.60). The reactions were carried out at 120° C., 130° C. and 140° C. and over a period of 20 minutes in each case. The SimDist results are provided in FIG. 7. Within this temperature range, no significant variation in results was observed.

Figure 8:
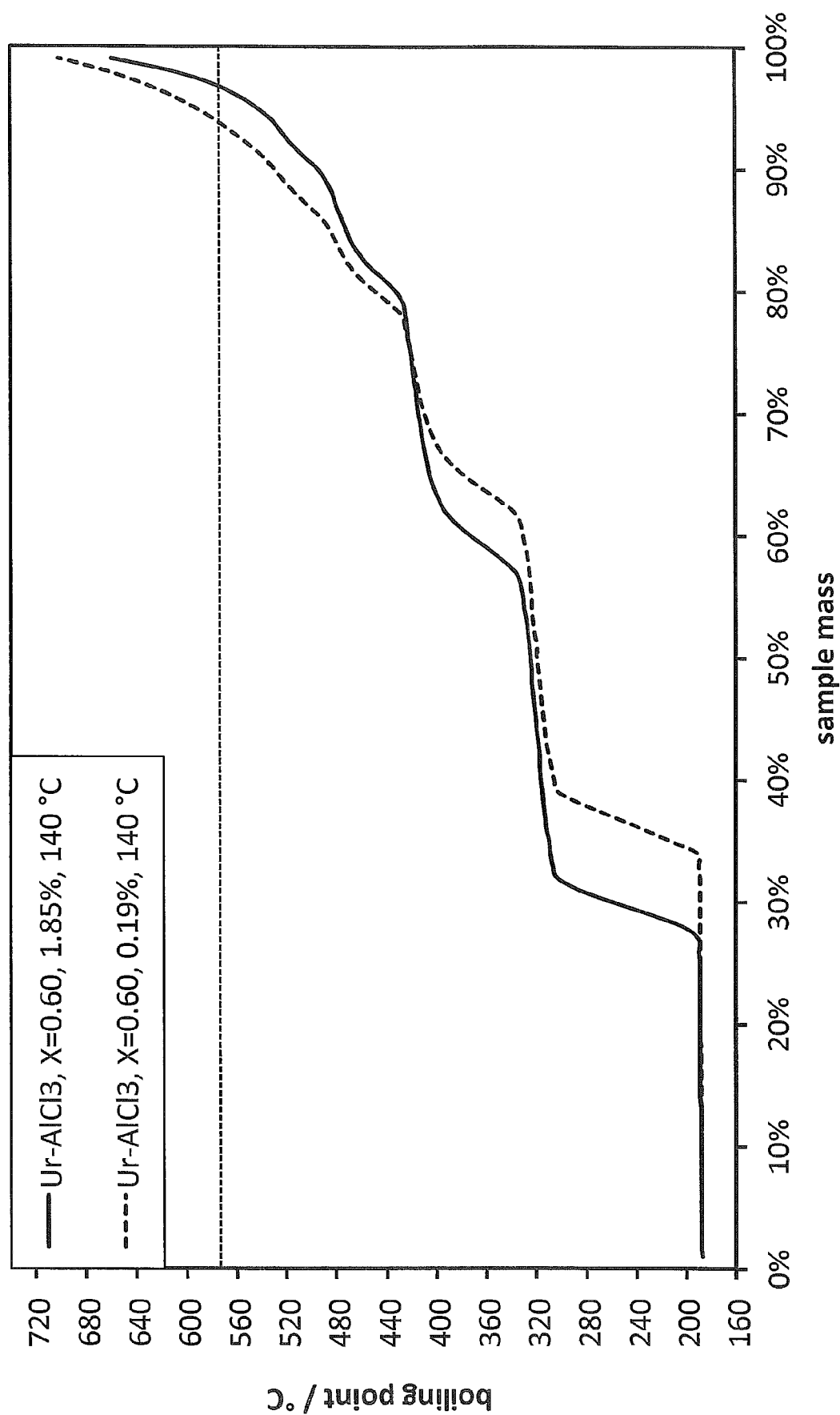
FIG. 8 shows the SimDist analyses of the product distributions obtained by oligomerising 1-decene in the presence of a LC prepared from $AlCl_3$ and urea ($\chi_{AlCl3}$=0.60) with catalyst loadings of 1.85 mol % and 0.19 wt %.

Example 10—Effect of Catalyst Loading in the LC Catalysed Oligomerisation of 1-Decene Oligomerisation of 1-decene was carried out according to the general procedure of Example 4 in the presence of a LC catalyst prepared from AlCl$_3$ and urea ($\chi_{AlCl3}$=0.60) and with catalyst loadings of 0.19 wt % and 1.85 wt %. The reaction was carried out at 140° C. and over a period of 20 minutes in the case of 1.85 wt % catalyst loading, and over a period of 30 minutes in the case of 0.19 wt % catalyst loading. The SimDist results are provided in FIG. 8. No significant difference in conversion was observed.

Figure 9:
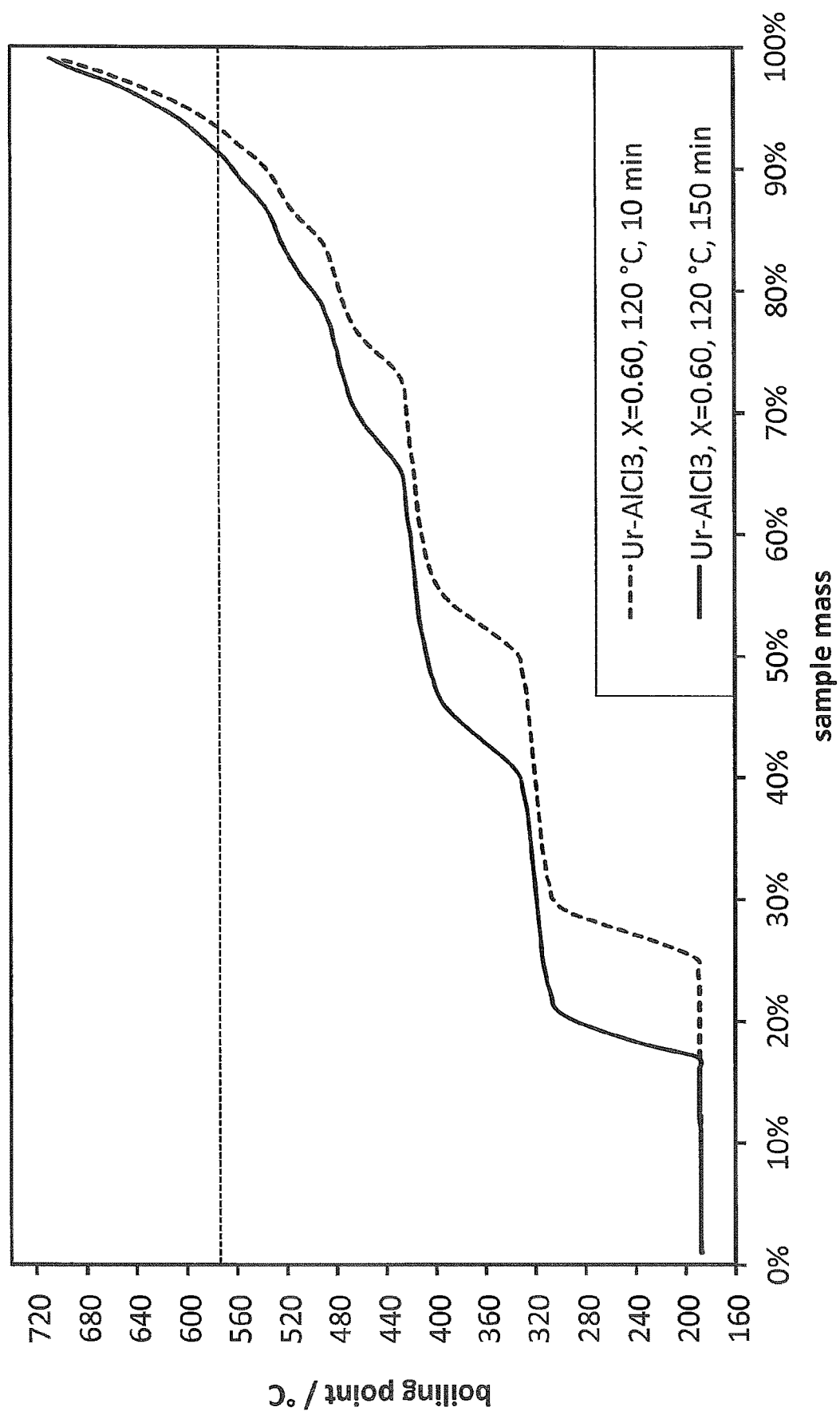
FIG. 9 shows the SimDist analyses of the product distributions obtained by oligomerising 1-decene in the presence of a LC prepared from $AlCl_3$ and urea ($\chi_{AlCl3}$=0.60) with reaction times of 10 minutes and 150 minutes.

Example 11—Effect of Reaction Time in the LC Catalysed Oligomerisation of 1-Decene Oligomerisation of 1-decene was carried out according to the general procedure of Example 4 in the presence of a LC catalyst prepared from AlCl$_3$ and urea ($\chi_{AlCl3}$=0.60) and over a period of 10 minutes and 150 minutes. The reaction temperature was 120° C. in each case and the catalyst loading was 0.93 wt %. The SimDist results are provided in FIG. 9. Although the reaction time was increased by a factor of 15, only a small increase in conversion was observed. The product distribution is substantially unchanged, however, with only a low level of heavies produced. The physical properties of the oligomeric product after removal of monomer and most of the dimer are provided in Table 3.

TABLE 3

| Reaction time | conversion | Kv$_{40}$ | Kv$_{100}$ | VI |
|---|---|---|---|---|
| 150 | 82 | 33.5271 | 5.7535 | 113 |
| 10 | 73 | 24.6905 | 4.7272 | 110 |

Figure 10:
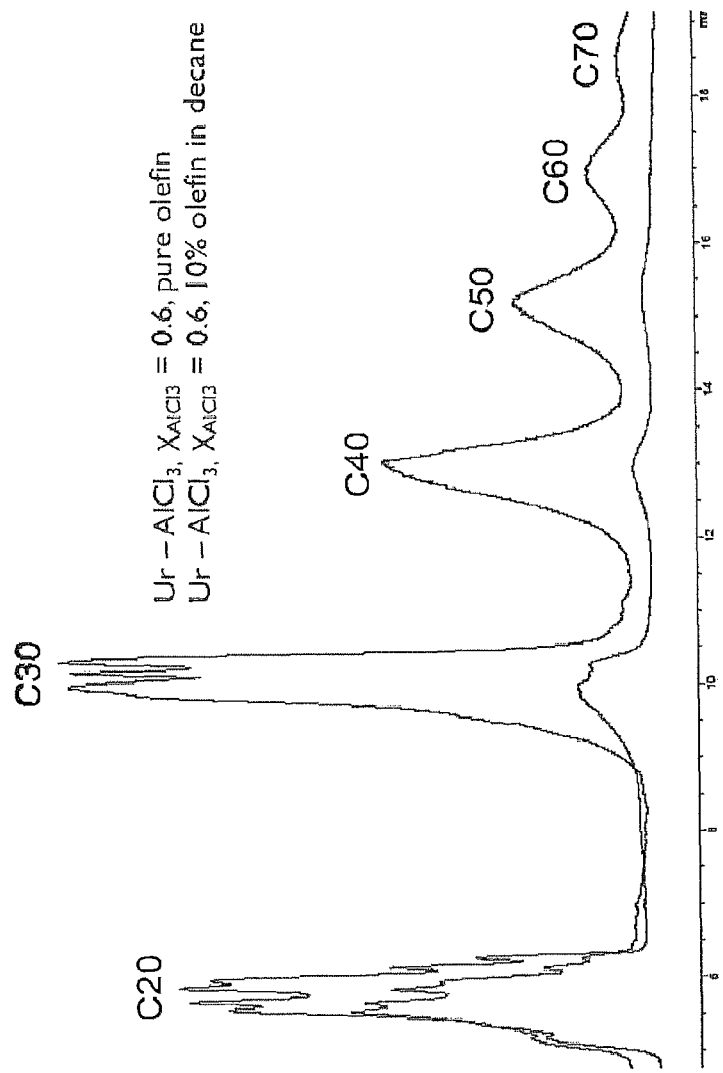
FIG. 10 shows the gas chromatograms of the products obtained by oligomerising pure 1-decene and 10 mol % 1-decene in decane in the presence of a LC prepared from $AlCl_3$ and urea ($\chi_{AlCl3}$=0.60).

Example 12—Effect of Paraffins in the Feedstock in the LC Catalysed Oligomerisation of 1-Decene Oligomerisation of 1-decene in the form of a mixture of 10 wt % decene in decane was carried out according to the general procedure of Example 4 in the presence of 1.85 wt % of a LC catalyst prepared from AlCl$_3$ and urea ($\chi_{AlCl3}$=0.60) and at a reaction temperature of 120° C. over a period of 20 minutes. The results are provided in FIG. 10 in the form of a gas chromatography (GC) trace alongside the result obtained using only 100% 1-decene as the feedstock under corresponding conditions. The presence of decane is observed to shift the product distribution towards shorter oligomers.

Example 13—Reproducibility of the LC Catalysed Oligomerisation of 1-Decene

Figure 11:
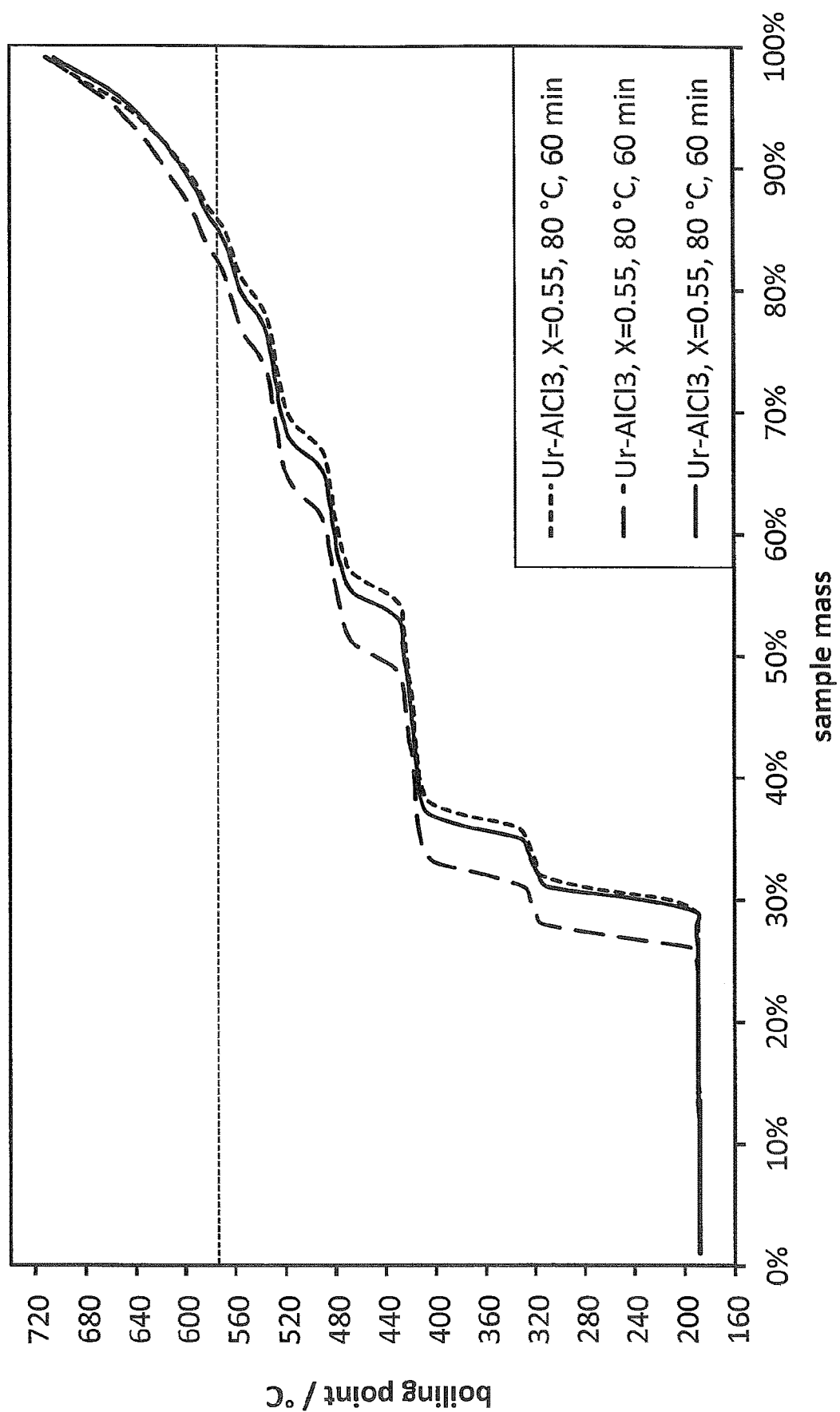
FIG. 11 shows the SimDist analyses of the product distributions obtained by oligomerising 1-decene in the presence of a LC prepared from $AlCl_3$ and urea ($\chi_{AlCl3}$=0.55) in parallel reactions.

Oligomerisation of 1-decene according to the general procedure of Example 4 was carried out in triplicate in the presence of 3.71 wt % of a LC catalyst prepared from AlCl$_3$ and urea ($\chi_{AlCl3}$=0.55). The reaction temperature was 80° C. and the reaction was conducted over a period of 1 hour. The SimDist results are provided in FIG. 11 and show excellent reproducibility, with minor variations in conversion believed to be due to the presence of trace amounts of water.

Example 14—Comparison to Commercial PAOs

Figure 12:
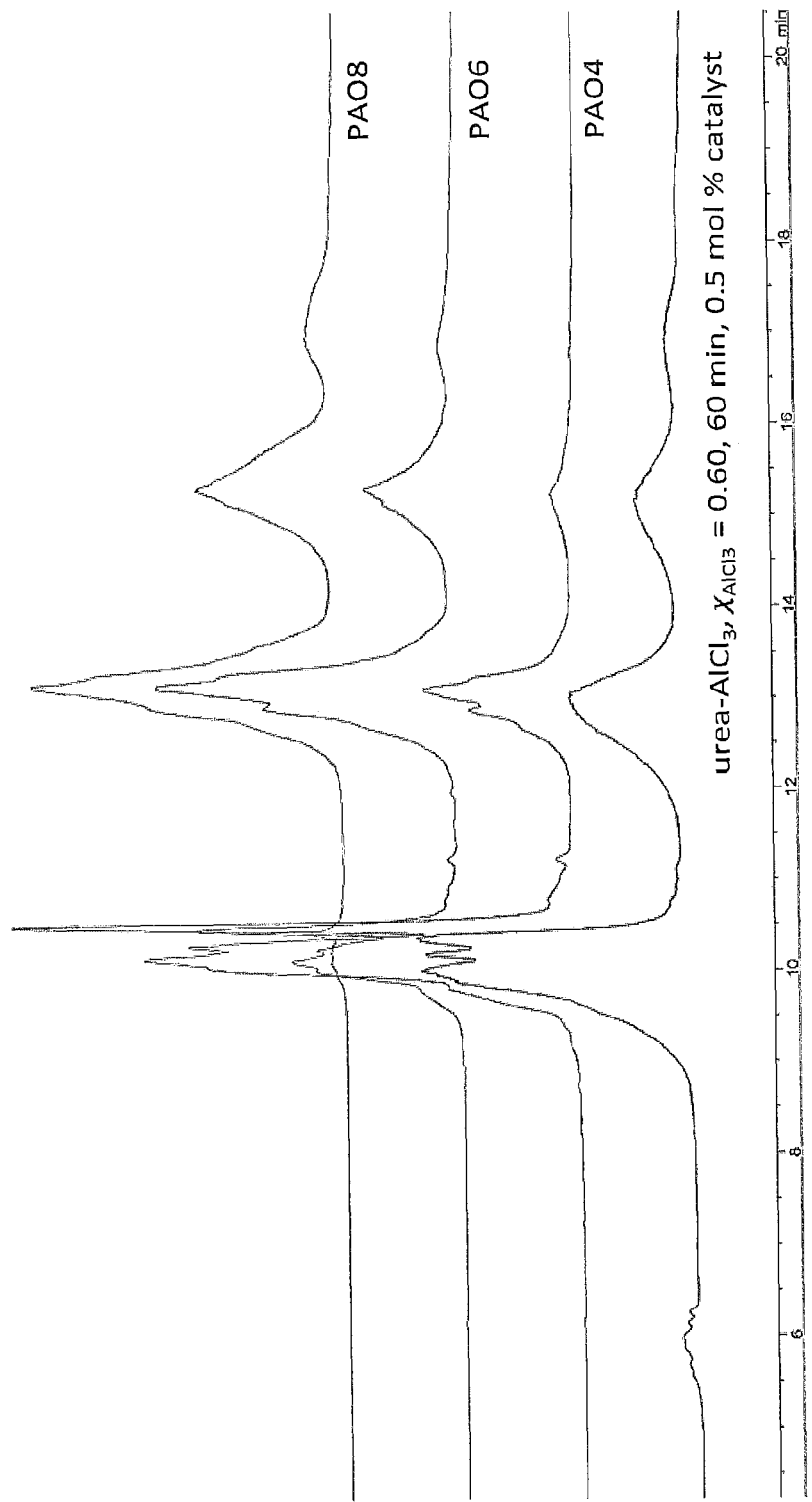
FIG. 12 shows the gas chromatogram of the product obtained by oligomerising 1-decene in the presence of a LC prepared from $AlCl_3$ and urea ($\chi_{AlCl3}$=0.60) compared to the gas chromatograms of commercial PAOs.
Figure 13:
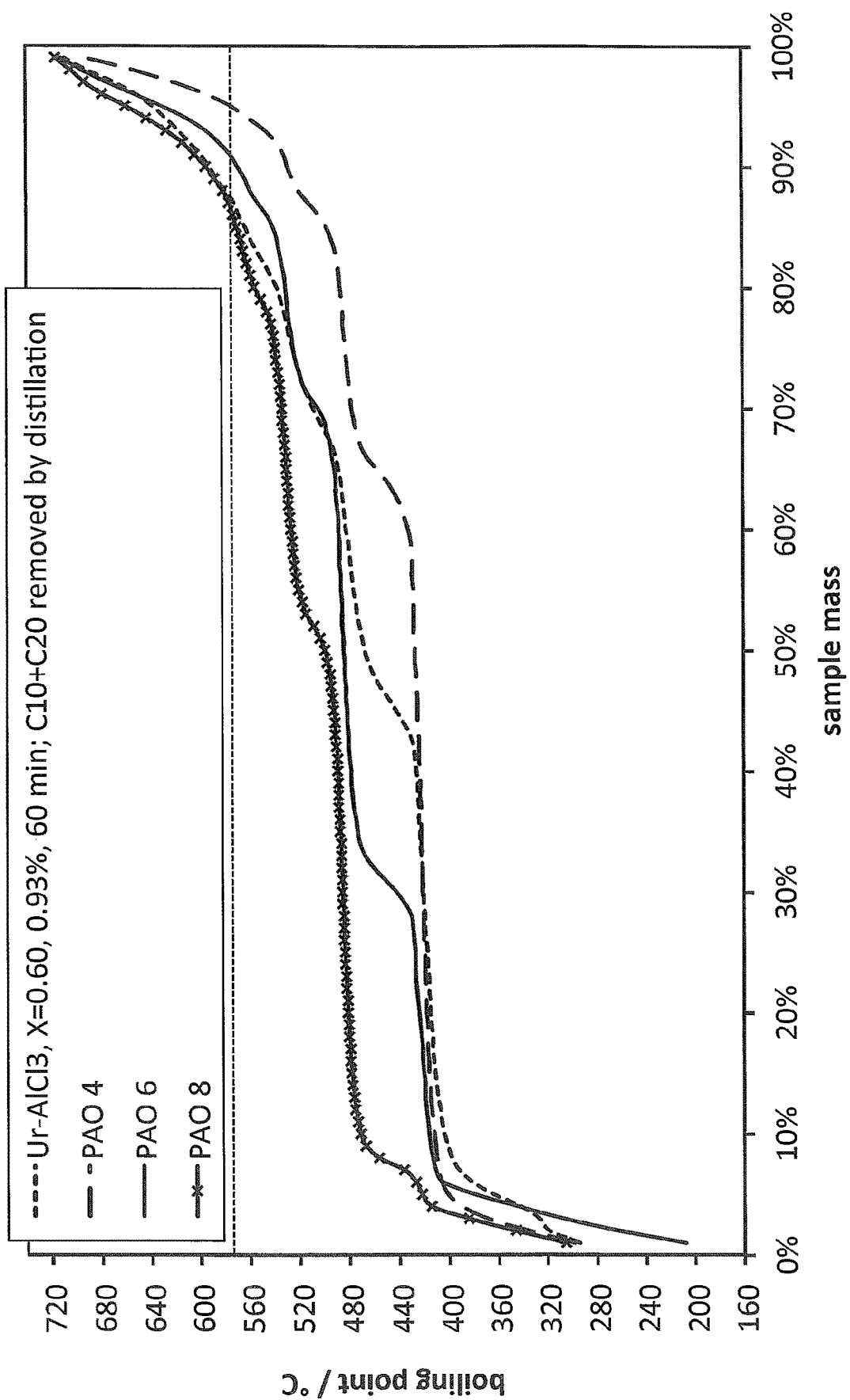
FIG. 13 shows the SimDist analysis of the product distribution obtained by oligomerising 1-decene in the presence of a LC prepared from $AlCl_3$ and urea ($\chi_{AlCl3}$=0.60) compared to the SimDist analyses of commercial PAOs.

The product of the oligomerisation of 1-decene prepared according to the general procedure of Example 4 in the presence of 0.93 wt % of a LC catalyst prepared from AlCl$_3$ and urea ($\chi_{AlCl3}$=0.60) at 120° C. and with a reaction time of 1 hour, was compared to commercial samples of PAO 4, 6 and 8. The product distribution of the oligomerised product obtained according to the process of the invention, following the removal of unreacted monomer and most of the dimer by distillation, was found to correspond closely to the product distribution of commercial PAOs, as shown by the GC traces in FIG. 12 and the SimDist results in FIG. 13.

Example 15—Oligomerisation of Mixed Alpha-Olefins Using LC Catalysts

An industrial alpha-olefin feedstock having a composition of 30% 1-decene, 50% 1-dodecene, 2% 1-tridecene, 12% 1-pentadecene and 6% C$_{18}$ 1-octadecene was carried out according to the general procedure of Example 4 in the presence of a LC catalyst prepared from AlCl$_3$ and urea ($\chi_{AlCl3}$=0.60) and at a range or reaction times, catalyst loadings and reaction temperatures. Due to the presence of higher alpha-olefins, lower reactivity and therefore the need for a more active system was anticipated. In view of the composition of the feedstock, the product would be expected to contain oligomers of various carbon numbers. Reaction conditions examined and the product distributions obtained are summarised in Table 4

TABLE 4

| Reaction time min | Catalyst loading wt % | Temp. ° C. | <C15 wt % | C15-C25 | C26-C35 | C36-C45 | C46-C55 |
|---|---|---|---|---|---|---|---|
|  |  |  |  | wt % of product |  |  |  |
| 120.0 | 0.19 | 120 | 76.0 | 20.0 | 3.0 | 1.0 | 0.0 |
| 120.0 | 0.37 | 120 | 54.0 | 24.0 | 10.0 | 6.0 | 2.0 |
| 120.0 | 0.37 | 120 | 54.0 | 26.0 | 12.0 | 6.0 | 2.0 |
| 120.0 | 0.37 | 120 | 53.0 | 26.0 | 12.0 | 7.0 | 2.0 |
| 120.0 | 1.85 | 120 | 30.0 | 27.0 | 23.0 | 14.0 | 6.0 |
| 60.0 | 5.56 | 140 | 14.0 | 26.0 | 31.0 | 28.0 | 1.0 |

As shown in Table 4, optimum conversion and product distribution was obtained at 140° C. and with a catalyst concentration of 3 mol %.

Example 16—Oligomerisation of C$_{16}$ Olefinic Feedstocks

The oligomerisation of 1-hexadecene was carried out according to the general procedure of Example 4 in the presence of a LC catalyst prepared from AlCl$_3$ and urea ($\chi_{AlCl3}$=0.60) and at a range or reaction times, catalyst loadings and reaction temperatures. Heavier alpha-olefins are less chemically active than alpha-olefins of lower molecular weight. Oligomerisation of heavier alpha-olefins is therefore expected to require a more active catalytic system. Reaction conditions examined and the product distributions obtained are summarised in Table 5.

TABLE 5

| Reaction time min | Catalyst loading wt % | temp. ° C. | conversion wt % | dimer | trimer | tetramer | >tetramer |
|---|---|---|---|---|---|---|---|
|  |  |  |  |  | wt % of product |  |  |
| 30.0 | 0.5 | 70 | 82.0 | 8.6 | 40.7 | 28.4 | 22.2 |
| 30.0 | 1.74 | 120 | 76.0 | 48.0 | 40.0 | 10.7 | 1.0 |
| 15.0 | 1.74 | 140 | 75.0 | 55.4 | 36.5 | 8.1 | 0.0 |
| 30.0 | 1.74 | 140 | 75.0 | 60.8 | 33.8 | 5.4 | 0.0 |
| 120.0 | 1.74 | 140 | 86.0 | 49.4 | 40.0 | 9.4 | 1.2 |
| 120.0 | 3.48 | 140 | 89.0 | 45.5 | 43.2 | 10.2 | 1.1 |
| 15.0 | 3.48 | 140 | 80.0 | 55.7 | 38.0 | 6.3 | 0.0 |
| 30.0 | 1.74 | 160 | 81.0 | 57.5 | 36.3 | 6.3 | 0.0 |

Example 17—Oligomerisation of $C_{18}$ Olefinic Feedstocks

The oligomerisation of 1-octadecene was carried out according to the general procedure of Example 4 in the presence of a LC catalyst prepared from $AlCl_3$ and urea ($\chi_{AlCl3}$=0.60) and at a range or reaction times, catalyst loadings and reaction temperatures. Reaction conditions examined and the product distributions obtained are summarised in Table 6.

TABLE 6

| Reaction time min | Catalyst loading wt % | temp. ° C. | conversion wt % | dimer | trimer | tetramer | >tetramer |
|---|---|---|---|---|---|---|---|
| | | | | | wt % of product | | |
| 15.0 | 1.55 | 140 | 77.0 | 55.3 | 36.8 | 7.9 | 0.0 |
| 15.0 | 3.09 | 140 | 78.0 | 53.2 | 39.0 | 7.8 | 0.0 |
| 20.0 | 0.21 | 160 | 43.0 | 78.6 | 21.4 | 2.4 | 0.0 |
| 20.0 | 1.03 | 160 | 50.0 | 53.1 | 34.7 | 12.2 | 0.0 |

Example 18—Oligomerisation of Mixed $C_{16}$ and $C_{18}$ Olefinic Feedstocks The oligomerisation of a 1:1 mixture by volume of 1-hexadecene and 1-octadecene was carried out according to the general procedure of Example 4 in the presence of a LC catalyst prepared from $AlCl_3$ and urea ($\chi_{AlCl3}$=0.60) at a catalyst concentration of 1.64 wt %. The reaction temperature was 140° C. and the reaction was carried out over a period of 60 minutes. Analysis of the product by SimDist showed 74.0% conversion of starting material and a product distribution of 57.7 wt % dimer, 35.6 wt % trimer and 6.8 wt % tetramer. The formation of higher oligomers was not observed.

Example 19—Oligomerisation of $C_{16}$ Olefinic Feedstocks

Figure 14:
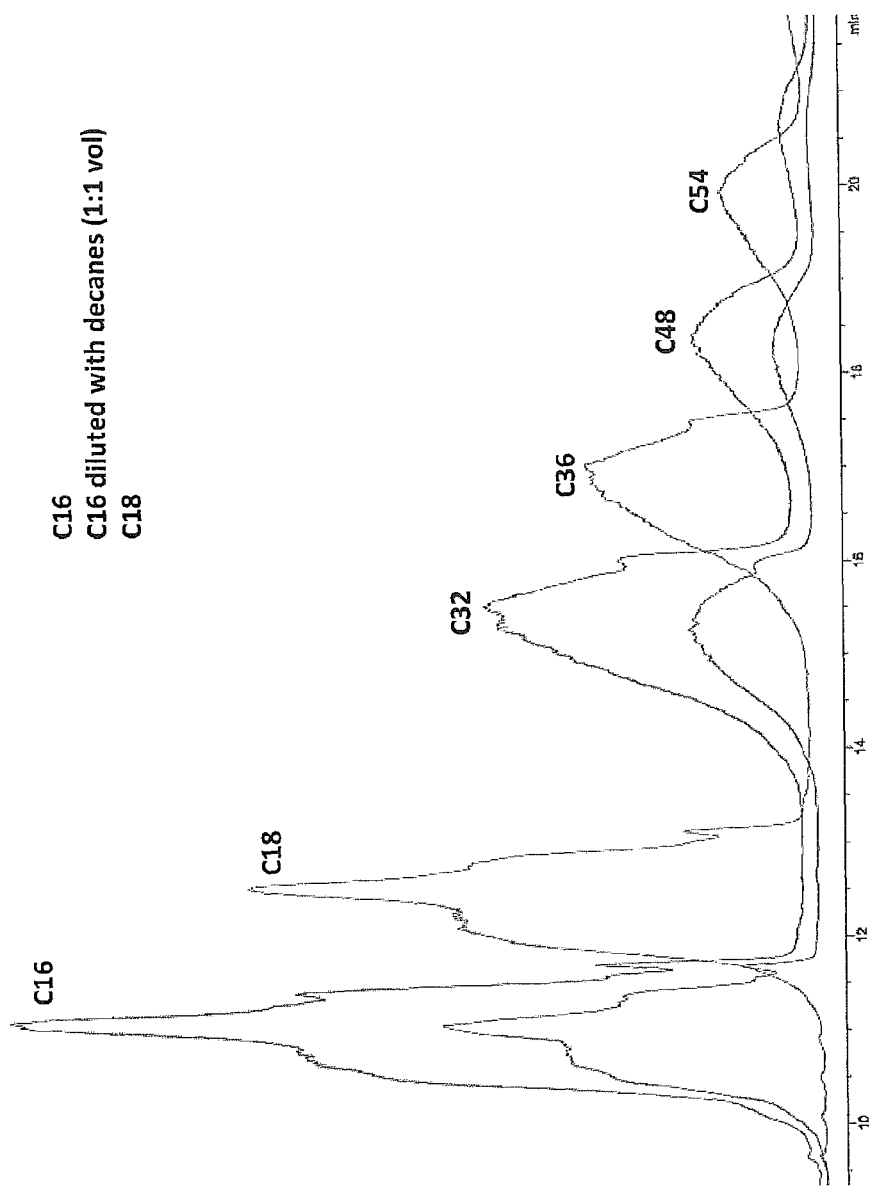
FIG. 14 shows the gas chromatograms of the products obtained by oligomerising $C_{16}$ alpha-olefins, $C_{16}$ alpha-olefins diluted with decane (1:1 by volume) and $C_{18}$ alpha-olefins in the presence of a LC catalyst prepared from $AlCl_3$ and urea ($\chi_{AlCl3}$=0.60).

The oligomerisation of a 1:1 mixture by volume of 1-hexadecene and decane was carried out according to the general procedure of Example 4 in the presence of a LC catalyst prepared from $AlCl_3$ and urea ($\chi_{AlCl3}$=0.60) at a catalyst concentration of 1.64 wt %. The reaction temperature was 140° C. and the reaction was carried out over a period of 20 minutes. Analysis of the product by SimDist showed 80.0% conversion of starting material and a product distribution of 59.0 wt % dimer and 41.0 wt % trimer. The presence of the paraffin decane in the reaction mixture is thus observed to suppress the formation of tetramers and higher oligomers from $C_{16}$ alpha-olefins. The SimDist gas chromatograms for products obtained according to Examples 16, 17 and 19 are provided as FIG. 14.

Reference Example 20—Oligomerisation of 1-Hexadecene Using [$C_2$mim][$Al_2Cl_7$]

Figure 15:
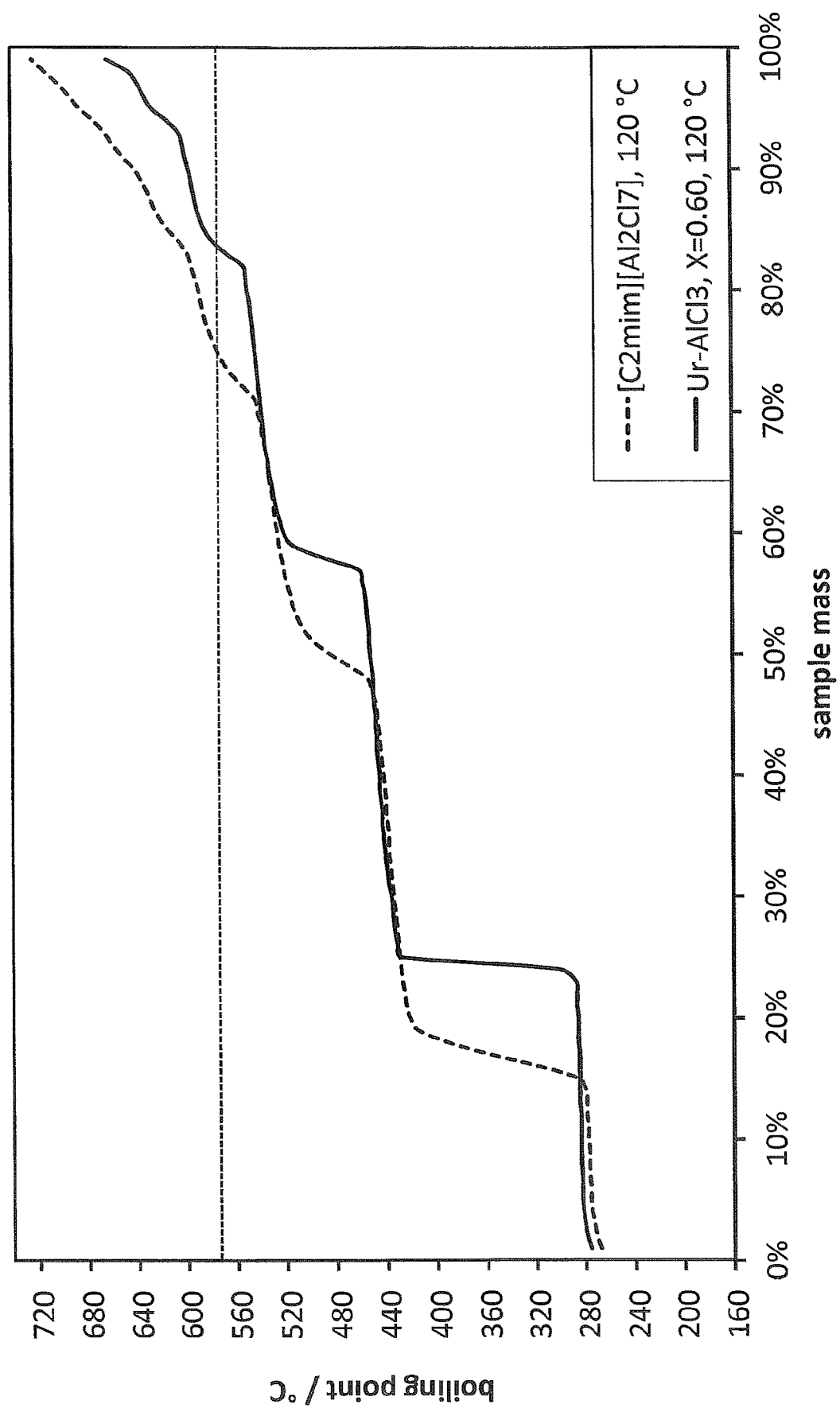
FIG. 15 shows the SimDist analysis of the product distribution obtained by oligomerising 1-hexadecene in the presence of the ionic liquid $[C_2mim][Al_2Cl_7]$ compared to the product distribution obtained using a LC catalyst prepared from $AlCl_3$ and urea (Ur) ($\chi_{AlCl3}$=0.60).

Oligomerisation of 1-decene was carried out in the presence of 1.5 wt % of the ionic liquid of Reference Example 1 according to the general procedure of Example 4 with a reaction temperature of 120° C. and a reaction time of 20 minutes. The results of the SimDist analysis are provided in FIG. 15.

Example 21—Oligomerisation of 1-Hexadecene Using LC Catalyst

Oligomerisation of 1-hexadecene was carried out according to the general procedure of Example 4 in the presence of a LC catalyst prepared from $AlCl_3$ and urea (Ur), ($\chi_{AlCl3}$=0.60). The reaction was carried out at 120° C. for a period of 20 minutes using 1.5 wt % of the LC catalyst. The results of the SimDist analysis are provided in FIG. 15 alongside the results for Reference Example 20. It is found that the LC system of the present invention provides an improved product distribution compared to the ionic liquid system.

Example 22—Physical Properties of Oligomeric Products

Oligomerisation of 1-decene was carried out according to the general procedure of Example 4 in the presence of a LC catalyst prepared from $AlCl_3$ and urea at a range of $\chi_{AlCl3}$ values, reaction times and catalyst loadings. The reaction temperature was 120° C. in each case. The physical properties of the oligomeric products obtained after removal of 1-decene monomer and most of the dimer are provided in Table 7.

TABLE 7

| $X_{AlCl3}$ | Time min | Catalyst mol % | $Kv_{40}$ cSt | $Kv_{100}$ cSt | VI | Pour Point ° C. |
|---|---|---|---|---|---|---|
| 0.550 | 20.0 | 1.000 | 25.4610 | 5.0124 | 125 | <−43 |
| 0.550 | 60.0 | 0.500 | 24.6813 | 5.0124 | 133 | <−43 |
| 0.600 | 60.0 | 0.500 | 27.2205 | 5.0796 | 115 | <−43 |
| 0.575 | 40.0 | 0.750 | 27.5310 | 5.2404 | 124 | <−43 |
| 0.600 | 20.0 | 0.500 | 23.1840 | 4.4741 | 104 | <−43 |
| 0.575 | 40.0 | 0.750 | 26.4056 | 5.0693 | 121 | <−43 |
| 0.575 | 40.0 | 0.750 | 32.3900 | 5.9206 | 129 | <−43 |
| 0.575 | 40.0 | 0.750 | 33.7870 | 5.9868 | 123 | <−43 |
| 0.575 | 40.0 | 1.170 | 40.8043 | 6.8576 | 126 | <−43 |
| 0.600 | 20.0 | 1.000 | 29.6286 | 5.7535 | 140 | <−43 |
| 0.617 | 40.0 | 0.750 | 33.7870 | 5.8313 | 115 | <−43 |
| 0.575 | 73.6 | 0.750 | 40.2845 | 6.7176 | 122 | <−43 |
| 0.550 | 20.0 | 0.500 | 24.1707 | 4.6806 | 111 | <−43 |
| 0.575 | 6.4 | 0.750 | 32.7474 | 5.8002 | 120 | <−43 |
| 0.575 | 40.0 | 0.750 | 30.9281 | 5.6447 | 124 | <−43 |
| 0.575 | 40.0 | 0.330 | 37.1657 | 6.3600 | 122 | <−43 |
| 0.575 | 40.0 | 0.750 | 27.5494 | 5.2248 | 123 | <−43 |
| 0.550 | 60.0 | 1.000 | 33.5271 | 5.8624 | 118 | <−43 |
| 0.600 | 60.0 | 1.000 | 56.3983 | 8.8635 | 134 | <−43 |

The invention claimed is:

1. A process for the preparation of alpha-olefin oligomers, comprising contacting an olefinic feedstock comprising $C_5$ to $C_{20}$ alpha-olefins with a liquid complex catalyst consisting essentially of:
   (i) at least one metal halide salt of the formula $MX_3$, wherein M is selected from aluminium and gallium, and each X is independently selected from chlorine, bromine and iodine; and
   (ii) at least one Lewis basic donor ligand containing a donor atom selected from oxygen, sulphur, nitrogen, phosphorus, arsenic and selenium;
   wherein the molar ratio of the at least one metal halide salt to the at least one Lewis basic donor ligand is in the range of from 1:1 to 4:1, and wherein the at least one Lewis basic donor ligand is selected from the group of compounds consisting of ketones, sulfoxides, phosphine-oxides, ureas, amides, thioketones, thioureas, thioamides, thioethers, amines, nitriles and phosphines; and
   wherein the contacting produces a product having a fraction which comprises dimers, trimers, and tetramers, wherein the product predominantly comprises the fraction.

2. The process according to claim 1, wherein M represents aluminium.

3. The process according to claim 2, wherein the molar ratio of the at least one metal halide salt to the at least one Lewis basic donor ligand is in the range of from 1:1 to 2:1.

4. The process according to claim 3, wherein the molar ratio of the at least one metal halide salt to the at least one Lewis basic donor ligand is from about 55:45 to about 65:35.

5. The process according to claim 4, wherein the molar ratio of the at least one metal halide salt to the at least one Lewis basic donor ligand is about 3:2.

6. The process according to claim 1, wherein X represents bromine or chlorine.

7. The process according to claim 6, wherein $MX_3$ represents $AlCl_3$.

8. The process according to claim 1, wherein the at least one Lewis basic donor ligand is selected from compounds having a formula selected from $R^1$—C(O)—$R^1$, $R^1$—S(O)—$R^1$, $R^2$NH—C(O)—NHR$^2$, $R^2$NH—C(S)—NHR$^2$, $R_1$—C(O)—NR$^2{}_2$, $(R^3)_3$P(O) and $R^1$—CN wherein:

each $R^1$ independently represents a $C_1$ to $C_{10}$ alkyl group;
$R^2$ is selected from hydrogen or a $C_1$ to $C_{10}$ alkyl group; and
$R^3$ represents a $C_4$ to $C_{10}$ alkyl group;
wherein any of $R^1$, $R^2$ and $R^3$ may optionally be substituted by one or more fluorine atoms.

9. The process according to claim 8, wherein the at least one Lewis basic donor ligand is selected from urea, N,N'-dimethylurea, N,N'-dimethylthiourea, acetamide, dimethylacetamide, acetone, dimethylsulfoxide and trioctylphosphine oxide.

10. The process according to claim 1, wherein the olefinic feedstock comprises at least 50 wt % of one or more $C_5$ to $C_{20}$ alpha-olefins.

11. The process according to claim 1, wherein the olefinic feedstock comprises at least 30 wt % $C_8$ to $C_{14}$ alpha-olefins.

12. The process according to claim 11, wherein the olefinic feedstock comprises at least 30 wt % 1-decene.

13. The process according to claim 11, wherein the olefinic feedstock comprises at least 30 wt % 1-dodecene.

14. The process according to claim 1, wherein the olefinic feedstock comprises at least 30 wt % $C_{16}$ to $C_{18}$ alpha-olefins.

15. The process according to claim 14, wherein the olefinic feedstock comprises at least 30 wt % 1-hexadecene.

16. The process according to claim 14, wherein the olefinic feedstock comprises at least 30 wt % 1-octadecene.

17. The process according to claim 1, wherein the olefinic feedstock is contacted with the liquid complex catalyst at a temperature of from 0 to 160° C.

18. The process according to claim 1, wherein the olefinic feedstock is contacted with the liquid complex catalyst at a pressure of from 10 to 1000 kPa.

19. The process according to claim 1, wherein the olefinic feedstock is contacted with from 0.01 to 5 wt % of the liquid complex catalyst based on the total weight of the liquid complex catalyst and olefinic feedstock.

20. The process according to claim 1, wherein the olefinic feedstock further includes paraffins.

* * * * *